(12) United States Patent
Kamal et al.

(10) Patent No.: US 9,273,039 B2
(45) Date of Patent: Mar. 1, 2016

(54) SYNTHESIS OF NEW BENZOTHIAZOLE DERIVATIVES AS POTENTIAL ANTI-TUBERCULAR AGENTS

(75) Inventors: Ahmed Kamal, Hyderabad (IN); Rajesh Vernc Shetti, Hyderabad (IN); Ponnampalli Swapna, Hyderabad (IN); Shaik Azeeza, Hyderabad (IN); A Malla Reddy, Hyderabad (IN); Inshad Ali Khan, Hyderabad (IN); Sheikh Tasduq Abdullah, Hyderabad (IN); Sandeep Sharma, Hyderabad (IN); Nitin Pal Kalia, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/232,407

(22) Filed: Sep. 14, 2011

(65) Prior Publication Data

US 2012/0095021 A1 Apr. 19, 2012

(30) Foreign Application Priority Data

Sep. 14, 2010 (IN) .......................... 2179/DEL/2010

(51) Int. Cl.
| | | |
|---|---|---|
| *C07D 277/82* | (2006.01) | |
| *A61K 31/426* | (2006.01) | |
| *C07D 417/12* | (2006.01) | |
| *C07D 417/14* | (2006.01) | |

(52) U.S. Cl.
CPC ............ *C07D 417/12* (2013.01); *C07D 417/14* (2013.01)

(58) Field of Classification Search
CPC ... C07D 277/68; C07D 277/82; A61K 31/426
USPC .................................. 548/152, 161; 514/367
See application file for complete search history.

(56) References Cited

U.S. PATENT DOCUMENTS

| | | | | |
|---|---|---|---|---|
| 2008/0039629 A1* | 2/2008 | Ramesh | ................ | A61K 31/428 546/156 |
| 2010/0056502 A1* | 3/2010 | Brown et al. | .............. | 514/224.2 |

OTHER PUBLICATIONS

Kamal et al.; "Anti-Tubercular Agents. Part 3. Benzothiadiazine as a Novel Scaffold for Anti-Mycobacterium Activity"; Bioorganic & Medicinal Chemistry 14 (2006); pp. 650-658.

Kamal et al.; "Antitubercular Agents. Part 1. Systhesis of Phthalimido-and Naphthalimido-linked Phenazines as New Prototype Antitubercular Agents"; Bioorganic & Medicinal Chemistry 15 (2005); pp. 1923-1926.

Kamal et al.; "Anti-Tubercular Agents. Part IV: Synthesis and Antimycobacterial Evaluation of Nitroheterocyclic-based 1,2,4-Benzothiadiazines"; Bioorganic & Medicinal Chemistry 17 (2006); pp. 5419-5422.

Koci et al.; "Hetercyclic Benzazole Derivatives with Antimycobacterial in Vitro Activity"; Bioorganic & Medicinal Chemistry 12 (2002); pp. 3275-3278.

Shi et al.; "Antitumour Benzothiazoles. Part 15. The Synthesis and Physico-Chemical Properties of 2-(4-Aminophenyl) Benzothiazole Sulfamate Salt Derivatives"; Bioorganic & Medicinal Chemistry Letters 11 (2001); pp. 1093-1095.

Rando et al.; "Potential Tuberculostatic Agents. Topliss Application on Benzoic Acid [(5-Nitro-thiophen-2-yl)-Methylene]-Hydrazide Series"; Bioorganic & Medicinal Chemistry 10 (2002); pp. 557-560.

Murugasu-Oei et al.; "Bactericidal Activity of Nitrofurans Against Growing and Dormant Mycobacterium Bovis BCG"; Journal of Antimicrobial Chemotherapy (2000) 46; pp. 917-919.

* cited by examiner

*Primary Examiner* — Scarlett Goon
*Assistant Examiner* — Sonya Wright
(74) *Attorney, Agent, or Firm* — Ohlandt, Greeley, Ruggiero & Perle, L.L.P.

(57) ABSTRACT

The present disclosure provides compounds of general formula A:

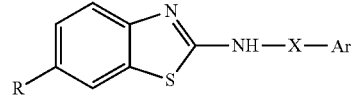

General Formula A useful as potential anti-tubercular agents.

3 Claims, 1 Drawing Sheet

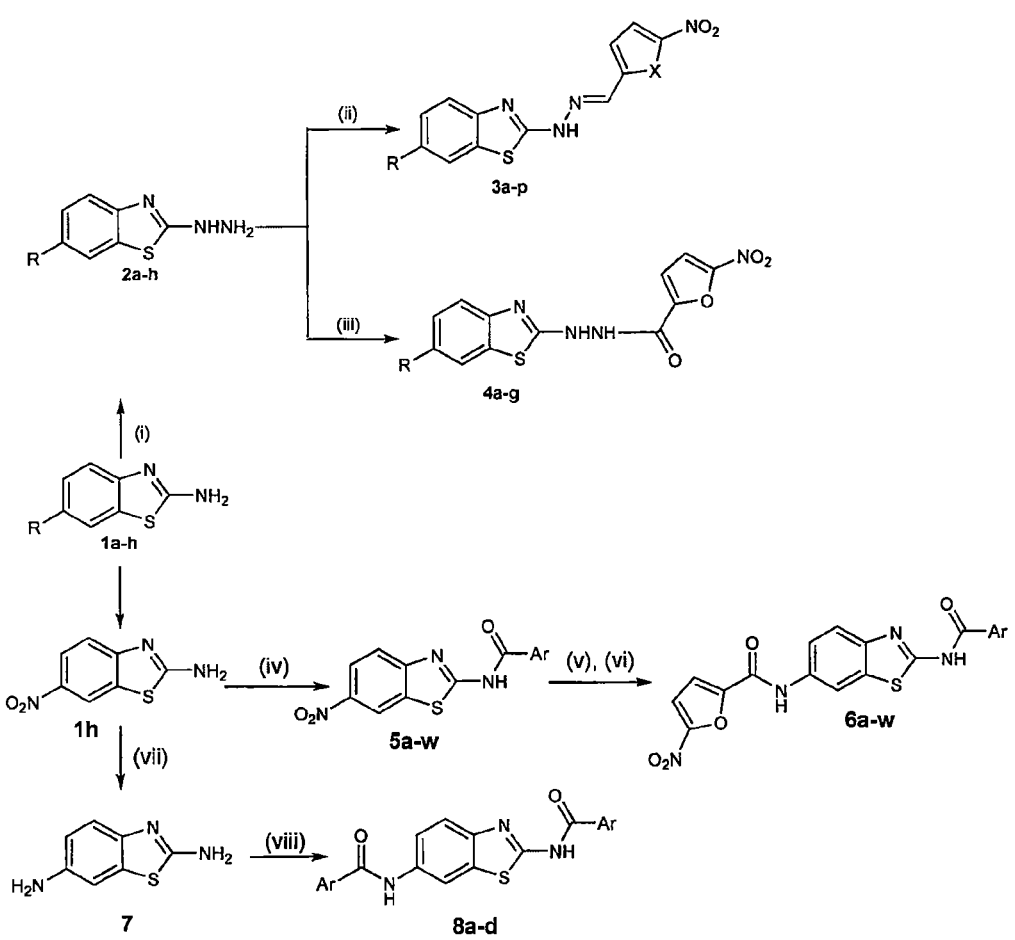

SYNTHESIS OF NEW BENZOTHIAZOLE DERIVATIVES AS POTENTIAL ANTI-TUBERCULAR AGENTS

BACKGROUND

1. Field of the Disclosure

The present disclosure relates to benzothiazole compounds as anti-tubercular chemotherapeutic agents and the process for the preparation thereof. Particularly, the present disclosure relates to 2,6-substituted benzothiazole compounds of general "formula A".

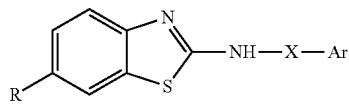

General Formula A

X=—N=CH—, —NH—CO—, —CO—
Ar=Phenyl, 4-methylphenyl, 4-methoxyphenyl, 4-trifluoromethylphenyl, 4-trifluoromethoxyphenyl, 4-fluorophenyl, 4-chlorophenyl, 2-chloro-3-methoxyphenyl, 3,5-dimethoxyphenyl, 3,4,5-trimethoxyphenyl, pyridyl, nicotenyl, isonicotinyl, 5-nitro-2-furyl, styryl, 4-fluorostyryl, 4-methylstyryl, 4-methoxystyryl, 4-trifluorostyryl, 4-trifluoromethoxystyryl, 5-nitro-2-furyl, 1-methyl-4-nitro-1H-2-pyrrolyl, 1-methyl-5-nitro-1H-2-imadazolyl, 1-methyl-3-nitro-1H-2-pyrazolyl
R=Hydro, Methyl, Methoxy, Trifluoromethyl, Trifluoromethoxy, Fluoro, Chloro, Nitro, 5-Nitrofuran-2-carboxamide, 5-Nitrothiophene-2-carboxamide, 1-methyl-4-nitro-1H-2-pyrrolcarboxamide, 1-methyl-5-nitro-1H-2-imadazolcarboxamide, 1-methyl-3-nitro-1H-2-pyrazolcarboxamide The structural formula of these benzothiazole compounds is given below and is represented by the following compounds of formula 3a-p, 4a-h, 6a-w and 8a-d.

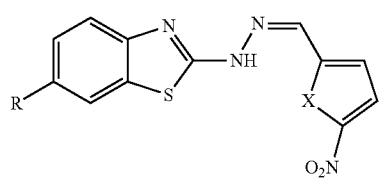

3a-p

R=H, CH₃, OCH₃, CF₃, OCF₃, F, Cl, NO₂
X=O, S

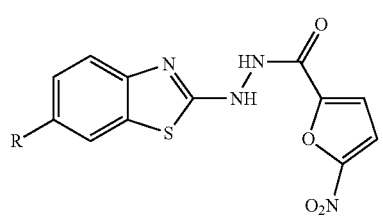

4a-h

R=H, CH₃, OCH₃, CF₃, OCF₃, F, Cl, NO₂

6a-w

Ar=Phenyl, 4-methylphenyl, 4-methoxyphenyl, 4-trifluoromethylphenyl, 4-trifluoromethoxyphenyl, 4-fluorophenyl, 4-chlorophenyl, 2-chloro-3-methoxyphenyl, 3,5-dimethoxyphenyl, 3,4,5-trimethoxyphenyl, pyridyl, nicotenyl, isonicotinyl, 5-nitro-2-furyl, styryl, 4-fluorostyryl, 4-methylstyryl, 4-methoxystyryl, 4-trifluorostyryl, 4-trifluoromethoxystyryl 8a-d Ar=5-nitro-2-furyl, 1-methyl-4-nitro-1H-2-pyrrolyl, 1-methyl-5-nitro-1H-2-imadazolyl, 1-methyl-3-nitro-1H-2-pyrazolyl

2. Discussion of the Background Art

As a part of investigation of new chemotherapeutic agents from this laboratory, over the past eight years our research efforts have been focused towards the intervention of new scaffolds with good antimycobacterial activity and eventually to develop new anti-tubercular agents that can improve the current therapeutic regimen as well as effective in the treatment of MDR-TB (Kamal, A.; Babu, A. H.; Ramana, A. V.; Sinha, R.; Yadav, J. S.; Arora, S. K. *Bioorg. Med. Chem. Lett.* 2005, 15, 1923-1926; Kamal, A.; Reddy, K. S.; Ahmed, S. K.; Khan, M. N. A.; Sinha, R. K.; Yadav, J. S.; Arora, S. K. *Bioorg. Med. Chem.* 2006, 14, 650-658; Kamal, A.; Ahmed, S. K.; Reddy, K. S.; Khan, M. N. A.; Shetti, R. V. C. R. N. C.; Siddhardha, B.; Murthy, U. S. N.; Khan, I. A.; Kumar, M.; Sharma, S.; Ram, A. B. *Bioorg. Med. Chem. Lett.* 2007, 17, 5419-5422).

In early 80s, diverse biological properties have been reported on benzothiazole scaffold including anti-tubercular activity by different research groups around the globe. (Palmer, P. J.; Trigg, R. B.; Warrington, J. V. *J. Med. Chem.* 1971, 14, 248; Katz. L.; *J. Med. Chem.* 1953, 75, 712; Palmer, P. J.; Ward, R. J.; Miyamastu, H.; Uneo, H.; Shimizu, H.; Hosono, J.; Tomari, M.; Seida, K.; Suzuki, T.; Wada, J. *J. Med. Chem.* 1974, 17, 491; Shi, D-. F.; Bradshaw, T. D.; Chua, M-. S.; Westwell, A. D.; Stevens M. F. G. *Bioorg. Med. Chem. Lett.* 2001, 11, 1093.

Klimesova and co-workers have developed the bezylsulfanyl moiety at C-2 position of benzothiazole with good antimycobacterial activity. Further, Schiff bases and hydrazones of benzothiazoles are also found to be active against *Mycobacterium tuberculosis* (Koci, J.; Klimesova, V.; Waisser, K.; Kaustova, J.; Dahsec, H.-M.; Mollmannc, U. *Bioor. Med. Chem. Lett.* 2002, 12, 3275; Katz. L.; *J. Am. Chem. Soc.* 1953, 75, 712). Recently Kozikowski and co-workers have developed the 2-methyl-5-amido benzothiazoles as potential antitubercular agents (Huang, Q.; Mao, J.; Wan, B.; Wang, Y.; Brim, R.; Franzblau, S. G.; Kozikowski, A. P.; *J. Med. Chem.* 2009, 52, 6757). These molecules are believed to inhibit the HisG enzyme of *Mycobacterium tuberculosis* (Cho, Y.; Ioerger, T. R.; Sacchettini, J. C. *J. Med. Chem.* 2008, 51, 5984). In addition nitrobenzothiazole amides have shown interesting anti-tubercular activity, by binding to HisG enzyme of M. tb (de Carvalho, L. P. S.; Lin, G.; Jiang, X.; Nathan, C. *J. Med. Chem.* 2009, 52, 5789; Dykhuizen, E. C.; May, J. F.; Tongpenyai, A.; Kiessling, L. L. *J. Am. Chem. Soc.* 2008, 130, 6706).

On the other hand, nitrofuran is an important scaffold in many potential anti-tubercular agents Lee, R. E., Tangapally, R. P., Yendapally, R., McNeil, M., Lenaerts, A. US 2005/0222408 A1; Tangallapally, R. P., Yendapally, R., Lee, R. E., Lenaerts, A. J. M., Lee, R. E., *J. Med. Chem.* 2005, 48, 8261.

Similarly, 5-nitrothiophene key intermediate in many active anti-tuberculosis compounds (Rando, D. G.; Sato, D. N.; Siqerira, L.; Malvezzi, A.; Leite, C. Q. F.; Amaral, A. T.; Ferreiraa, E. I.; Tavaresa, L. C.; *Bioorg. Med. Chem.* 2002, 10, 557; Murugasu-Oei, B.; Dick, T. *J. Antimicrob. Chemother.* 2000, 46, 917). These findings have encouraged us for the design and synthesis of new nitrofuran/nitrothiophene conjugated benzothiazoles and subsequently evaluated for activity against tubercular cultures.

The main object of the disclosure is to provide the new benzothiazole compounds as useful anti-tubercular chemotherapeutics.

Another object of the present disclosure is to provide a process for the synthesis of these new benzothiazole compounds as useful chemotherapeutic agent against sensitive and MDR-strains of TB.

Another object of the present disclosure is to provide a new mechanistic anti-tubercular agents against sensitive and MDR strains of tubercle bacilli.

Another object of the present disclosure is to provide new compounds based on the benzothiazole scaffold in good yields.

SUMMARY OF THE DISCLOSURE

Accordingly, the present disclosure provides benzothiazole compounds as anti-tubercular chemotherapeutic agents and the process for the preparation thereof.

In one embodiment of the present disclosure, benzothiazole compounds of general formulae A General Formula A

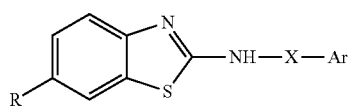

X=—N=CH—, —NH—CO—, —CO—
Ar=Phenyl, 4-methylphenyl, 4-methoxyphenyl, 4-trifluoromethylphenyl, 4-trifluoromethoxyphenyl, 4-fluorophenyl, 4-chlorophenyl, 2-chloro-3-methoxyphenyl, 3,5-dimethoxyphenyl, 3,4,5-trimethoxyphenyl, pyridyl, nicotenyl, isonicotinyl, 5-nitro-2-furyl, styryl, 4-fluorostyryl, 4-methylstyryl, 4-methoxystyryl, 4-trifluorostyryl, 4-trifluoromethoxystyryl, 5-nitro-2-furyl, 1-methyl-4-nitro-1H-2-pyrrolyl, 1-methyl-5-nitro-1H-2-imadazolyl, 1-methyl-3-nitro-1H-2-pyrazolyl
R=Hydro, Methyl, Methoxy, Trifluoromethyl, Trifluoromethoxy, Fluoro, Chloro, Nitro, 5-Nitrofuran-2-carboxamide, 5-Nitrothiophene-2-carboxamide, 1-methyl-4-nitro-1H-2-pyrrolcarboxamide, 1-methyl-5-nitro-1H-2-imadazolcarboxamide, 1-methyl-3-nitro-1H-2-pyrazolcarboxamide In another embodiment of the present disclosure, benzothiazole compounds of general formulae is represented by the compounds of general formula 3a-p, 4a-h, 6a-w and 8a-d.

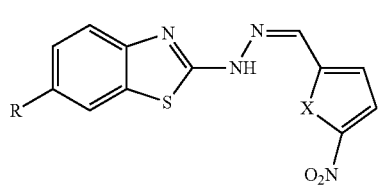

3a-p

R=H, $CH_3$, $OCH_3$, $CF_3$, $OCF_3$, F, Cl, $NO_2$
X=O, S

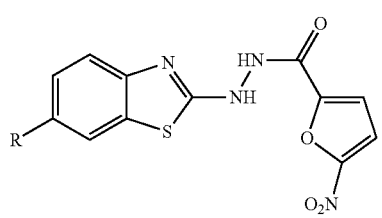

4a-h

R=H, $CH_3$, $OCH_3$, $CF_3$, $OCF_3$, F, Cl, $NO_2$

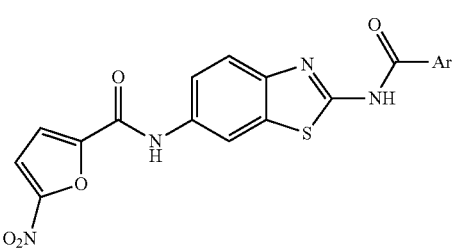

6a-w

Ar=Phenyl, 4-methylphenyl, 4-methoxyphenyl, 4-trifluoromethylphenyl, 4-trifluoromethoxyphenyl, 4-fluorophenyl, 4-chlorophenyl, 2-chloro-3-methoxyphenyl, 3,5-dimethoxyphenyl, 3,4,5-trimethoxyphenyl, pyridyl, nicotenyl, isonicotinyl, 5-nitro-2-furyl, styryl, 4-fluorostyryl, 4-methylstyryl, 4-methoxystyryl, 4-trifluorostyryl, 4-trifluoromethoxystyryl

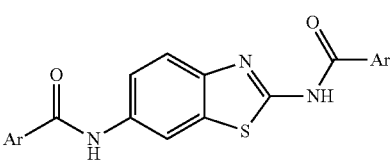

8a-d

Ar=5-nitro-2-furyl, 1-methyl-4-nitro-1H-2-pyrrolyl, 1-methyl-5-nitro-1H-2-imadazolyl, 1-methyl-3-nitro-1H-2-pyrazolyl
In another embodiment of the present disclosure, benzothiazole compounds of general formula A, wherein the structural formula of the representative compounds are:
3a). 5-nitro-2-furaldehyde 2-(1,3-benzothiazole-2-yl)hydrazone;
3b). 5-nitro-2-thiophenecarbaldehyde 2-(1,3-benzothiazole-2-yl)hydrazone;
3c). 5-nitro-2-furaldehyde 2-(6-methyl-1,3-benzothiazole-2-yl)hydrazone;
3d). 5-nitro-2-thiophenecarbaldehyde 2-(6-methyl-1,3-benzothiazole-2-yl)hydrazone;
3e). 5-nitro-2-furaldehyde 2-(6-methoxy-1,3-benzothiazole-2-yl) hydrazone;
3f). 5-nitro-2-thiophenecarbaldehyde 2-(6-methoxy-1,3-benzothiazole-2-yl)hydrazone;
3g). 5-nitro-2-furaldehyde 2-(6-trifluoromethyl-1,3-benzothiazole-2-yl)hydrazone;
3h). 5-nitro-2-thiophenecarbaldehyde 2-(6-trifluoromethyl-1,3-benzothiazole-2-yl)hydrazone;
3i). 5-nitro-2-furaldehyde 2-(6-trifluoromethoxy-1,3-benzothiazole-2-yl)hydrazone;
3j). 5-nitro-2-thiophenecarbaldehyde 2-(6-trifluoromethoxy-1,3-benzothiazole-2-yl)hydrazone;
3k). 5-nitro-2-furaldehyde 2-(6-fluoro-1,3-benzothiazole-2-yl)hydrazone;
3l). 5-nitro-2-thiophenecarbaldehyde 2-(6-fluoro-1,3-benzothiazole-2-yl)hydrazone;
3m). 5-nitro-2-furaldehyde 2-(6-chloro-1,3-benzothiazole-2-yl)hydrazone;
3n). 5-nitro-2-thiophenecarbaldehyde 2-(6-chloro-1,3-benzothiazole-2-yl)hydrazone;
3o). 5-nitro-2-furaldehyde 2-(6-nitro-1,3-benzothiazole-2-yl)hydrazone;
3p). 5-nitro-2-thiophenecarbaldehyde 2-(6-nitro-1,3-benzothiazole-2-yl)hydrazone;
4a). N'2-(1,3-benzothiazol-2-yl)-5-nitro-2-furancarbohydrazide;
4b). N'2-(6-methyl-1,3-benzothiazol-2-yl)-5-nitro-2-furancarbohydrazide;
4c). N'2-(6-methoxy-1,3-benzothiazol-2-yl)-5-nitro-2-furancarbohydrazide;
4d). N'2-(6-trifluoromethyl-1,3-benzothiazol-2-yl)-5-nitro-2-furancarbohydrazide;
4e). N'2-(6-trifluoromethoxy-1,3-benzothiazol-2-yl)-5-nitro-2-furanecarbohydrazide;
4f). N'2-(6-fluoro-1,3-benzothiazol-2-yl)-5-nitro-2-furanecarbohydrazide;
4g). N'2-(6-chloro-1,3-benzothiazol-2-yl)-5-nitro-2-furanecarbohydrazide;
4h). N'2-(6-nitro-1,3-benzothiazol-2-yl)-5-nitro-2-furanecarbohydrazide;
6a). N2-[2-(benzoylamino)-1,3-benzothiazol-6-yl]-5-nitrofuramide;
6b). N2-{2-[(4-methylbenzoyl)amino]-1,3-benzothiazol-6-yl}-5-nitrofuramide;
6c). N2-{2-[(4-methoxybenzoyl)amino]-1,3-benzothiazol-6-yl}-5-nitrofuramide;
6d). N2-{2-[(4-trifluoromethylbenzoyl)amino]-1,3-benzothiazol-6-yl}-5-nitrofuramide;
6e). N2-{2-[(4-trifluoromethoxybenzoyl)amino]-1,3-benzothiazol-6-yl}-5-nitrofuramide;
6f). N2-{2-[(4-fluorobenzoyl)amino]-1,3-benzothiazol-6-yl}-5-nitrofuramide;
6g). N2-{2-[(4-chlorobenzoyl)amino]-1,3-benzothiazol-6-yl}-5-nitrofuramide;
6h). N2-{2-[(2-chloro-3-methoxybenzoyl)amino]-1,3-benzothiazol-6-yl}-5-nitrofuramide;
6i). N2-{2-[(2,4-difluorobenzoyl)amino]-1,3-benzothiazol-6-yl}-5-nitrofuramide;
6j). N2-{2-[(2,4-dichlorobenzoyl)amino]-1,3-benzothiazol-6-yl}-5-nitrofuramide;
6k). N2-{2-[(3,5-dimethoxybenzoyl)amino]-1,3-benzothiazol-6-yl}-5-nitrofuramide;
6l). N2-{2-[(3,4,5-trimethoxybenzoyl)amino]-1,3-benzothiazol-6-yl}-5-nitrofuramide;
6m). N5-(6-{[5-nitro-2-furyl)carbonyl]amino}-1,3-benzothiazol-2-yl)-1,3-benzodioxole-5-carboxamide;
6n). N4-(6-{[(5-nitro-2-furyl)carbonyl]amino}-1,3-benzothiazol-2-yl)isonicotinamide;
6o). N3-(6-{[(5-nitro-2-furyl)carbonyl]amino}-1,3-benzothiazol-2-yl)nicotinamide;
6p). N2-(6-{[(5-nitro-2-furyl)carbonyl]amino}-1,3-benzothiazol-2-yl)-2-pyrazinecarboxamide;
6q). N2-(2-{[(E)-3-phenyl-2-propenoyl]amino}-1,3-benzothiazol-6-yl}-5-nitro-2-furamide;
6r). N2-(2-{[(E)-3-(4-methylphenyl)-2-propenoyl]amino}-1,3-benzothiazol-6-yl}-5-nitro-2-furamide;
6s). N2-(2-{[(E)-3-(4-methoxyphenyl)-2-propenoyl]amino}-1,3-benzothiazol-6-yl}-5-nitro-2-furamide;
6t). N2-(2-{[(E)-3-(4-trifluoromethylphenyl)-2-propenoyl]amino}-1,3-benzothiazol-6-yl}-5-nitro-2-furamide;
6u). N2-(2-{[(E)-3-(4-trifluoromethoxyphenyl)-2-propenoyl]amino}-1,3-benzothiazol-6-yl}-5-nitro-2-furamide;
6v). N2-(2-{[(E)-3-(4-fluorophenyl)-2-propenoyl]amino}-1,3-benzothiazol-6-yl)-5-nitro-2-furamide;
6w). N2-(2-{[(E)-3-(4-chlorophenyl)-2-propenoyl]amino}-1,3-benzothiazol-6-yl}-5-nitro-2-furamide;
8a). N2-(2-{[(5-nitro-2-furyl)carbonyl]amino}-1,3-benzothiazol-6-yl}-5-nitro-2-furamide;
8b). N2-(2-{[(1-methyl-4-nitro-1H-2-pyrrolyl)carbonyl]amino}-1,3-benzothiazol-6-yl}-1-methyl-4-nitro-1H-2-pyrrolcarboxamide;
8c). N2-(2-{[(1-methyl-5-nitro-1H-2-imadazolyl)carbonyl]amino}-1,3-benzothiazol-6-yl}-1-methyl-5-nitro-1H-2-imadazolecarboxamide;
8d). N2-(2-{[(1-methyl-3-nitro-1H-2-pyrazolyl)carbonyl]amino}-1,3-benzothiazol-6-yl}-1-methyl-3-nitro-1H-2-pyrazolecarboxamide;

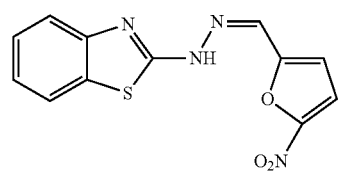

3a

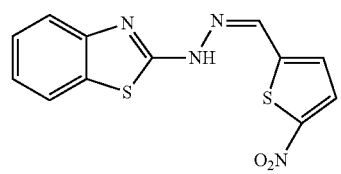

3b

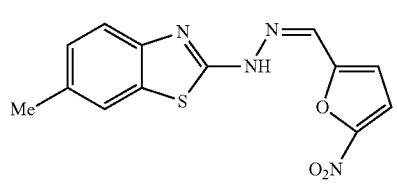

3c

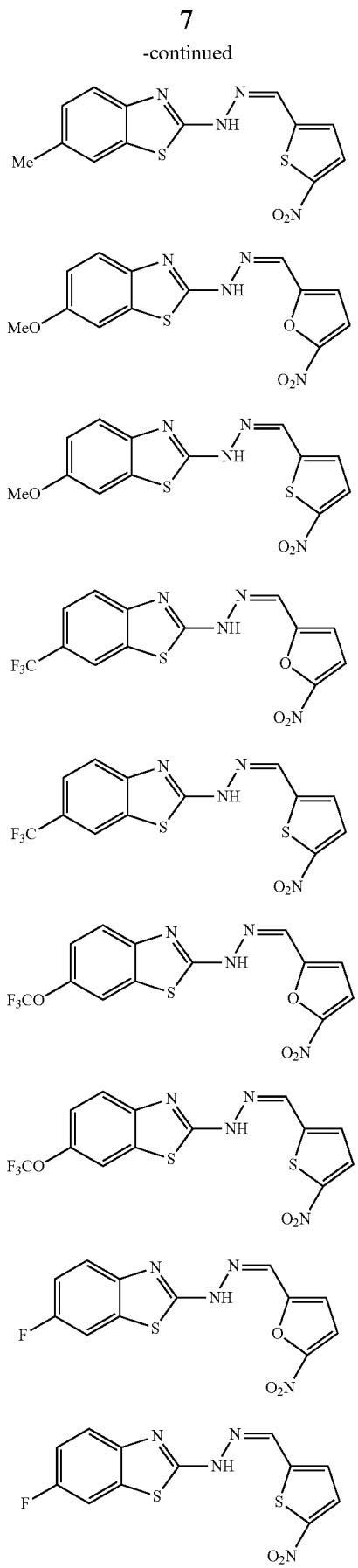
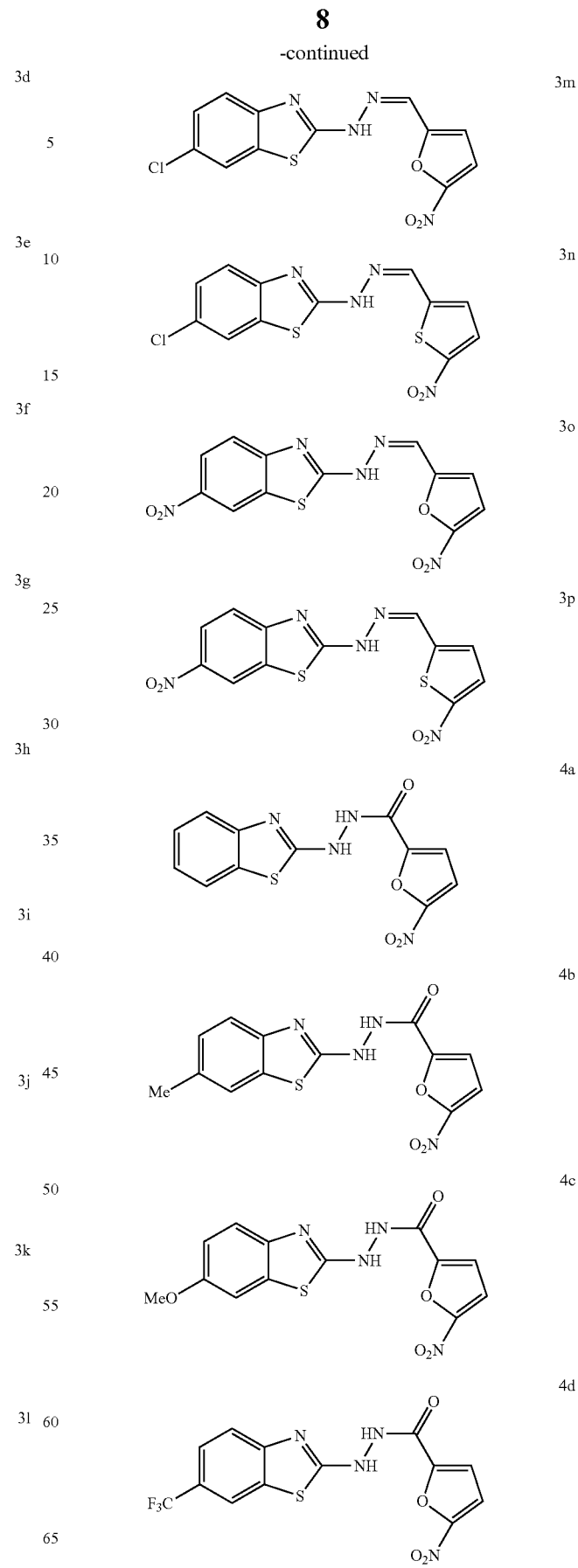

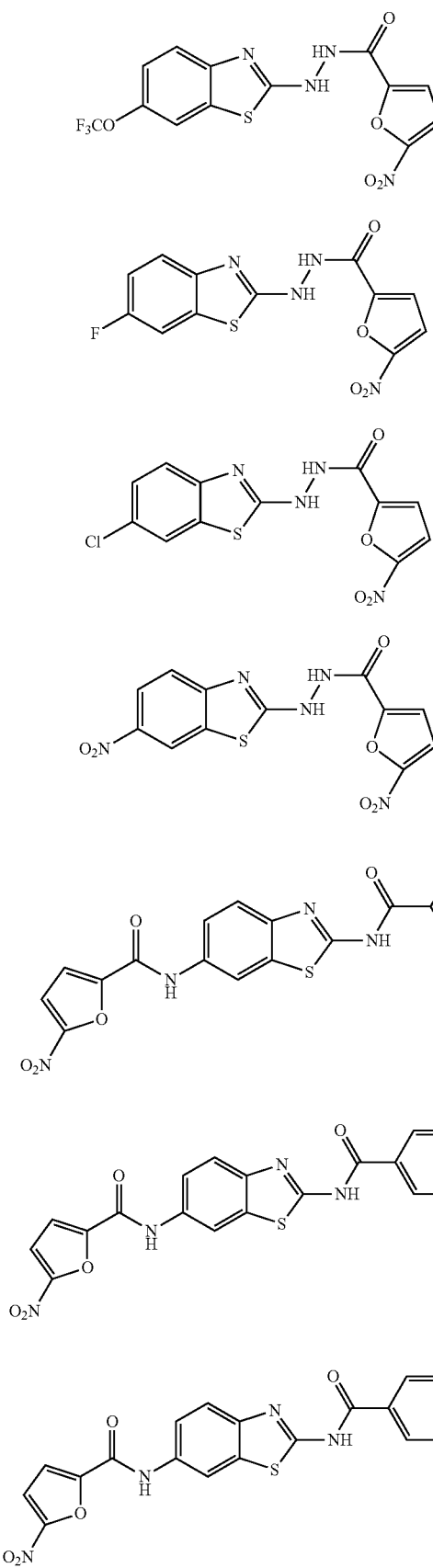
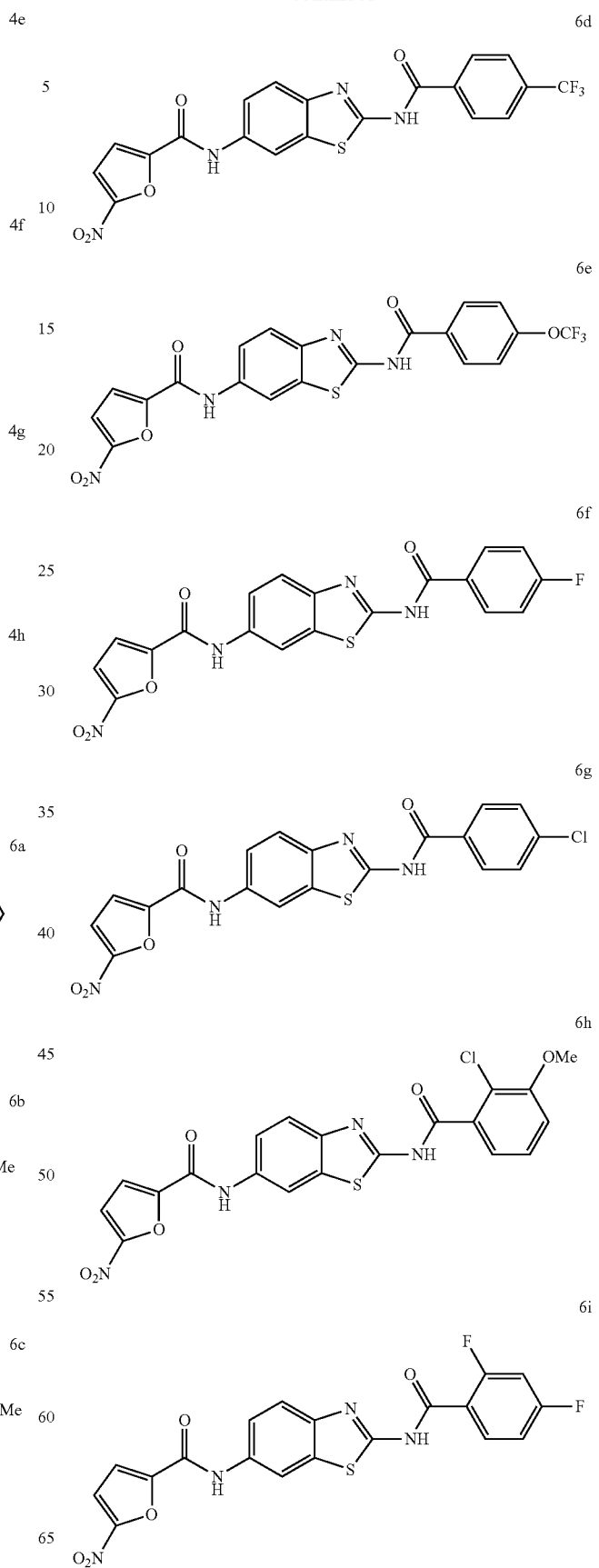

6j
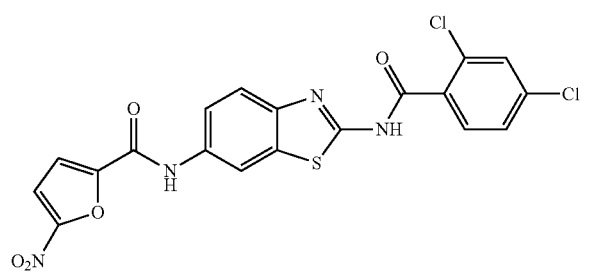
6k
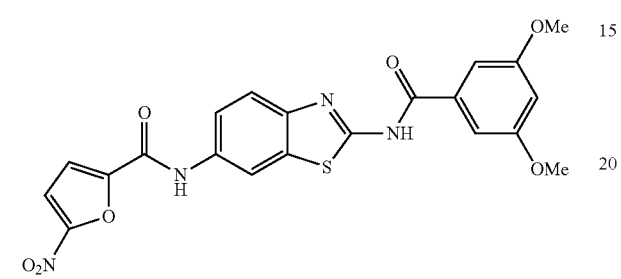
6l
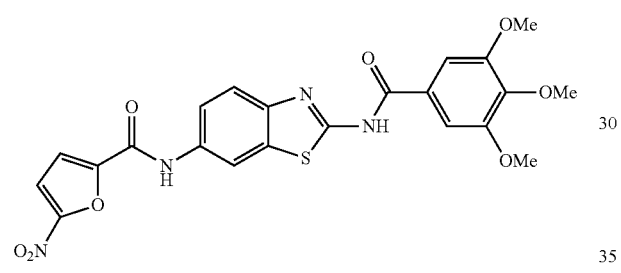
6m
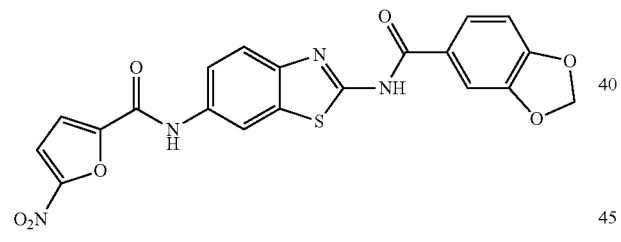
6n
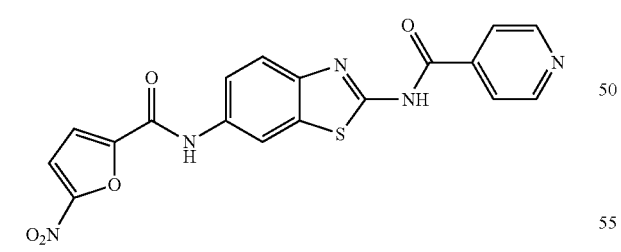
6o
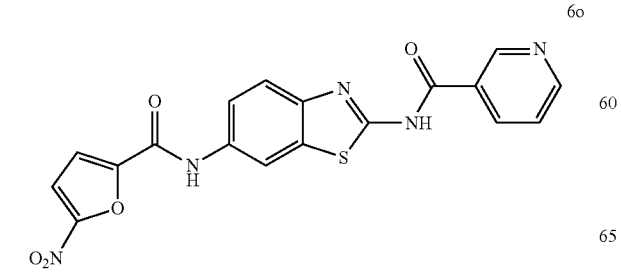
6p
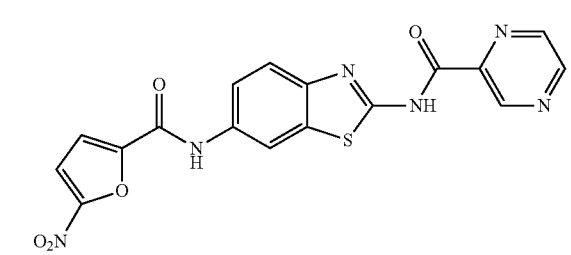
6q
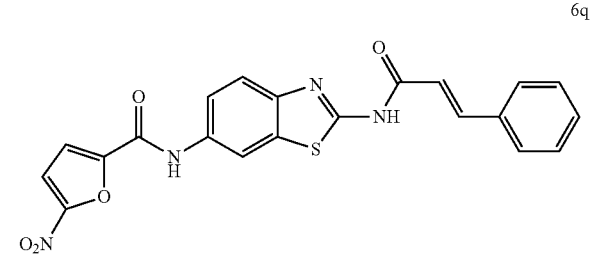
6r
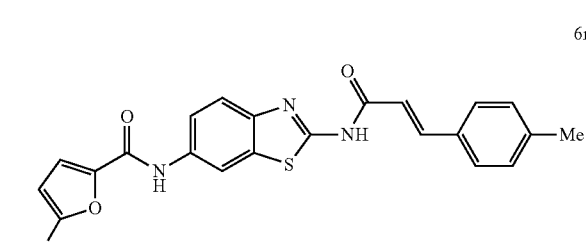
6s
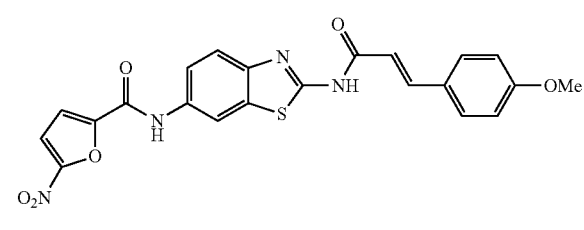
6t
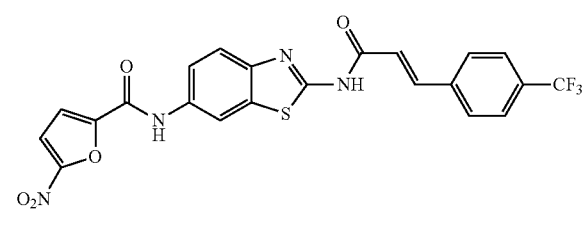
6u
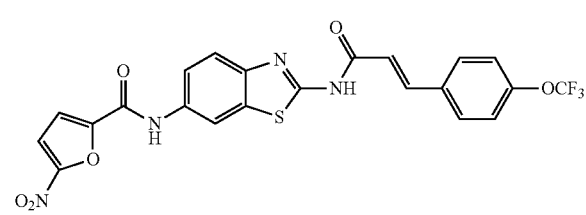

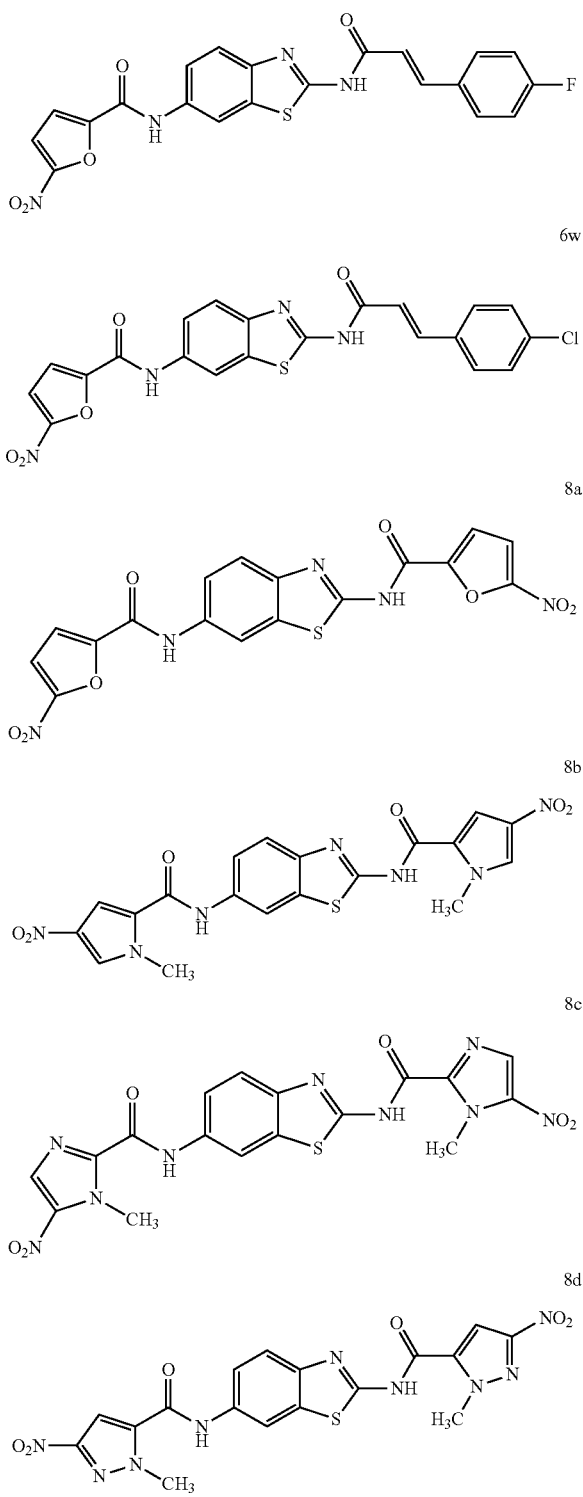

In another embodiment of the present disclosure, benzothiazole compounds of general formula A are useful as anti-tubercular agents.

In another embodiment of the present disclosure, benzothiazole compounds of general formula A for the treatment of tuberculosis wherein the representative compounds 3a-p, 4a-h, 6a, 6f, 6g, 6i, 6o, 6p, 6q, 6w, 8a showed in vitro activity against *M. tuberculosis* $H_{37}RV$ in a MIC range of 16 μg/mL-0.5 μg/mL.

In another embodiment of the present disclosure, benzothiazole compounds of general formula A for the treatment of tuberculosis wherein the representative compound 3j, 4e, 6a, 6f, 6g, 6i, 6o, 6p, 6q, 6w showed no cytotoxicity on being tested on AML-12 cell lines.

In another embodiment of the present disclosure, a pharmaceutical composition comprising a compound selected from the group of general formula A and a pharmaceutically acceptable carrier.

In another embodiment of the present disclosure, a method for treating a mycobacterial infection wherein said method comprises administering a composition to a patient in need thereof.

In another embodiment of the present disclosure, a process for the preparation of benzothiazole compounds of general formula 3a-p and 4a-h, wherein the said process comprises the steps of:
 i) dissolving substituted aldehydes or 5-nitro-2-furancarboxylic acid chloride and 2-hydrazeno-benzothiazoles in mol ratio ranging between 1:1 to 1:1.5 in a solvent to obtain reaction mixture a or reaction mixture b respectively;
 ii) adding acetic acid into the reaction mixture a as obtained in step (i) followed by stirring at temperature ranges between 65° C. to 75° C. for 2-3 hrs to obtain compounds of 3a-p;
 iii) treating reaction mixture b as obtained in step (i) with triethylamine and N,N dimethylaminopyridine followed by stirring at temperature ranges between 0° C.-30° C. for 12-14 hrs to obtain compounds of 4a-h.

In another embodiment of the present disclosure, a process wherein substituted aldehyde used in step (i) is selected from the group consisting of 5-nitro-2-furancarboxaldehyde, 5-nitro-2-thiophencarboxaldehyde, 5-nitro-2-nitrothiophen carboxaldehyde, 5-nitrofuran aldehyde and 5-nitrothiophen aldehyde.

In another embodiment of the present disclosure, a process wherein 2-hydrazeno-benzothiazoles used in step (i) is selected from the group consisting of 2-hydrazino-6-methyl-benzothiazoles, 2-hydrazino-6-methoxy-benzothiazoles, 2-hydrazino-6-trifluoromethyl-benzothiazole, 2-hydrazino-6-trifluoromethyl-benzothiazole, 2-hydrazino-6-trifluoromethyl-benzothiazole, 2-hydrazino-6-trifluoromethoxy-benzothiazole, 2-hydrazino-6-fluoro-benzothiazole, 2-hydrazino-6-chloro-benzothiazole, 2-hydrazino-6-nitro-benzothiazole and 2-hydrazino-6-chloromethoxybenzothiazole.

In another embodiment of the present disclosure a process wherein solvent used in step (i) is selected from the group consisting of ethanol and dry DMF.

In another embodiment of the present disclosure, a process for the preparation of benzothiazole compounds of general formula 6a-w and 8a-d, wherein the said process comprises the steps of:
 a) dissolving benzoylchloride or substitute carboxylic acid with substituted benzothiazole selected from the group consisting of 2-amino-6-nitrobenzothiazole, 2,6-diaminobenzothiazole in dry DMF to obtain reaction mixture;
 b) treating a reaction mixture as obtained in step (a) with triethylamine or 1-[3-(dimethylamino)propyl]-3-ethylcarbodiimide hydrochloride (EDCI) and N,N-dimethylaminopyridine (DMAP) followed by stirring at 0° C. to 30° C. for a period ranging between 12-14 hrs to obtain compound of 8(a-d) and compounds 5(a-w);
 c) dissolving compounds 5 (a-w) as obtained in step (b) in THF followed by adding ammonium formate and Zn dust;

d) stirring the reaction mixture as obtained in step (c) at temperature ranging between 25-30° C. for a period ranging between 30 min to 90 min. to obtain corresponding amine;

e) reacting corresponding amine as obtained in step (d) with dry DMF, 5-nitro-2-furoicacid, EDC (1-[3-(dimethylamino)propyl]-3-ethylcarbodiimide) and HoBt (1-hydroxy-1,2,3-benzotriazole) followed by stirring at temperature ranging between 25-30° C. for a period ranging between 12-14 hrs to obtain compounds 6a-w.

In another embodiment of the present disclosure, a process wherein substituted carboxylic acid used in step (a) is selected from the group consisting of 5-Nitro-2-furancarboxylic acid, 1-methyl-4-nitro-1H-pyrrole-2-carboxylic acid and 1-methyl-5-nitro-1H-imidazole-2-carboxylic acid.

In another embodiment of the present disclosure, wherein yield of the compounds ranges between 50%-89%.

BRIEF DESCRIPTION OF THE DRAWING

FIG. 1 discloses the process for the synthesis of new benzothiazole compounds as anti-tubercular agents producing the new compounds of benzothiazole scaffold in good yields. Reagents and conditions: (i) hydrazine hydrate, $N_2H_4.HCl$, glycol, 140° C., 4 h; (ii) 5-nitro-2-furaldehyde/5-nitro-2-thiophenaldehyde, EtOH, cat AcOH, reflux, 2 h; (iii) $Et_3N$, 5-nitro-2-furoic acid chloride, N,N-dimethyl formamide, THF (tetrahydrofuran), 25° C., 12 h; (iv) aryl acid, N,N-dimethyl formamide, EDC (1-Ethyl-3-(3-Dimethylaminopropyl)carbodiimide), HoBT (1-hydroxy-1,2,3-benzotriazole), 12 h; (v) Zn-ammonium formate, MeOH, rt, 1 h; (vii) 5-nitro-2-furoic acid, N,N-dimethyl formamide, EDC (1-Ethyl-3-(3-Dimethylaminopropyl)carbodiimide), HoBt (1-hydroxy-1,2,3-benzotriazole), 12 h; (viii) nitro-hetero acids, N,N-dimethyl formamide, EDC (1-Ethyl-3-(3-Dimethylaminopropyl)carbodiimide), HoBt (1-hydroxy-1,2,3-benzotriazole), 12 h.

DETAILED DESCRIPTION OF THE PREFERRED EMBODIMENT

The process for the synthesis of new benzothiazole compounds as anti-tubercular agents produces the new compounds of benzothiazole scaffold in good yields, wherein the key step for the synthesis of these compounds is by direct coupling of substituted heteroaromatic aldehydes with 2-hydrazido benzothiazole scaffold via amide linkage and hydrazine bridges.

Thus the present disclosure provides new class of benzothiazole compounds, which were synthesized by coupling reaction manner.

A program was initiated in the laboratory for the design and synthesis of new benzothiazole compounds with enhanced anti-tubercular activity against sensitive and MDR-resistant strains. In these efforts new benzothiazole scaffold based congeners have been synthesized and evaluated for their cytotoxicity and anti-tubercular potency compared to rifampicin. The synthesis of these compounds has been carried out as described in the Scheme-1 using substituted 2-amino benzothiazoles as starting material.

EXPERIMENTAL

The following examples are given by way of illustration of the present disclosure and therefore should not be construed to limit the scope of the present disclosure.

Example 1

General Procedure for the Synthesis of Synthesis of Aryl/heterocyclic aldehyde-2-(1,3-benzothiazol-2-yl)hydrazones (3a-p)

Aryl or heterocyclic aldehydes (1 mmol) and 2-hydrazenobenzothiazoles (1 mmol) were dissolved in ethanol (10 ml), to this resulting mixture catalytic amount of acetic acid (1 ml) was added and the mixture was stirred at 70° C. for 2 h, and the formed precipitate was collected by filtration and washed with cold methanol (3×30 mL) and chloroform (2×20 mL). The collected precipitate was recrystalysed from hot methanol affords hydrazones.

5-nitro-2-furaldehyde 2-(1,3-benzothiazole-2-yl) hydrazone (3a)

The compound 3a was prepared according to above described method by using 5-nitro-2-furancarboxaldehyde (140 mg, 1 mmol) and 2-hydrazeno-benzothiazoles (165 mg, 1 mmol) at 70° C. for 2 h (yield 244 mg, 85%).
$^1$H NMR (DMSO-$d_6$, 200 MHz): δ 12.3 (bs, 1H), 7.84 (m, 1H), 7.8 (s, 1H), 7.7 (d, 1H, J=3.7 Hz), 7.60 (d, 1H), 7.43 (m, 1H, J=2.9, 8.0 Hz), 7.22 (d, 1H, J=8.7 Hz), 6.90 (d, 1H, J=3.7 Hz); ESIMS: m/z 288 (M)$^+$, 289 (M+H)$^+$.

Example 2

5-nitro-2-thiophenecarbaldehyde 2-(1,3-benzothiazol-2-yl)hydrazone (3b)

The compound 3b was prepared according to above described method by using 5-nitro-2-thiophencarboxaldehyde (156 mg, 1 mmol) and 2-hydrazino-benzothiazoles (165 mg, 1 mmol) at 70° C. for 2 h (yield 258 mg, 85%).
$^1$H NMR (DMSO-$d_6$, 200 MHz): δ 12.0 (bs, 1H), 7.83 (d, 1H, J=4.3 Hz), 7.79 (s, 1H), 7.35 (d, 1H, J=8.0 Hz), 7.19-7.15 (m, 3H, J=4.3, 7.1 Hz), 7.00 (dd, 1H, J=8.0, 2.9 Hz); ESIMS: m/z 304 (M)$^+$, 305 (M+H)$^+$.

Example 3

5-nitro-2-furaldehyde 2-(6-methyl-1,3-benzothiazol-2-yl)hydrazone (3c)

The compound 3c was prepared according to above described method by using 5-nitro-2-furancarboxaldehyde (140 mg, 1 mmol) and 2-hydrazino-6-methyl-benzothiazoles (178 mg, 1 mmol) at 70° C. for 2 h (yield 268 mg, 89%).
$^1$H NMR (DMSO-$d_6$, 200 MHz): δ 11.4 (bs, 1H), 7.90 (s, 1H), 7.56 (d, 1H, J=3.7 Hz), 7.30 (d, 1H, J=9.0 Hz), 7.24 (d, 1H, J=2.2 Hz), 7.01 (d, 1H, J=3.7 Hz), 6.84 (dd, 1H, J=9.0, 2.2 Hz), 2.76 (s, 3H); ESIMS: m/z 302 (M)$^+$, 303 (M+H)$^+$.

Example 4

5-nitro-2-thiophenecarbaldehyde 2-(6-methyl-1,3-benzothiazol-2-yl)hydrazone (3d)

The compound 3d was prepared according to above described method by using 5-Nitro-2-nitrothiophen carboxaldehyde (157 mg, 1 mmol) and 2-hydrazino-6-methyl-benzothiazoles (178 mg, 1 mmol) at 70° C. for 2 h (yield 276 mg, 87%).
$^1$H NMR (DMSO-$d_6$, 200 MHz): δ 11.0 (bs, 1H), 7.80 (s, 1H), 7.81 (d, 1H, J=4.7 Hz), 7.32 (d, 1H, J=9.0 Hz), 7.25 (d, 1H, J=2.2 Hz), 7.17 (d, 1H, J=4.7 Hz), 7.00 (dd, 1H, J=9.0, 2.25 Hz), 2.74 (s, 3H); ESIMS: m/z 318 (M)+.

Example 5

5-nitro-2-furaldehyde 2-(6-methoxy-1,3-benzothiazol-2-yl)hydrazone (3e)

The compound 3e was prepared according to above described method by using 5-nitro-2-furancarboxaldehyde (140 mg, 1 mmol) and 2-hydrazino-6-methoxy-benzothiazoles (195 mg, 1 mmol) at 70° C. for 2 h (yield 283 mg, 89%).

$^1$H NMR (DMSO-d$_6$, 200 MHz): δ 12.4 (bs, 1H), 7.96 (s, 1H), 7.58 (d, 1H, J=3.7 Hz), 7.35 (d, 1H, J=9.0 Hz), 7.27 (d, 1H, J=2.2 Hz), 6.96 (d, 1H, J=3.7 Hz), 6.84 (dd, 1H, J=9.0, 2.2 Hz), 3.76 (s, 3H); ESIMS: m/z 318 (M)+, 319 (M+H)+.

Example 6

5-nitro-2-thiophenecarbaldehyde 2-(6-methoxy-1,3-benzothiazol-2-yl)hydrazone (3f)

The compound 3f was prepared according to above described method by using 5-Nitro-2-nitrothiophen carboxaldehyde (157 mg, 1 mmol) and 2-hydrazino-6-methoxy-benzothiazoles (195 mg, 1 mmol) at 70° C. for 2 h (yield 267 mg, 80%).

$^1$H NMR (DMSO-d$_6$, 200 MHz): δ 12.0 (bs, 1H), 7.89 (s, 1H), 7.82 (d, 1H, J=4.7 Hz), 7.30 (d, 1H, J=9.0 Hz), 7.27 (d, 1H, J=2.2 Hz), 7.19 (d, 1H, J=4.7 Hz), 6.84 (dd, 1H, J=9.0, 2.25 Hz), 3.76 (s, 3H); ESIMS: m/z 334 (M)+, 334 (M+H)+.

Example 7

5-nitro-2-furaldehyde 2-(6-trifluoromethyl-1,3-benzothiazol-2-yl)hydrazone (3g)

The compound 3g was prepared according procedure described for 3a by employing 5-nitrofuran aldehyde (141 mg, 1 mmol) and 2-hydrazino-6-trifluoromethyl-benzothiazole (233 mg, 1 mmol) at 70° C. for 2 h (yield 302 mg, 85%).

$^1$H NMR (DMSO-d$_6$, 200 MHz): δ 11.5 (bs, 1H), 7.84 (m, 1H, J=4.3 hz), 7.60 (d, 1H), 7.58 (d, 1H, J=3.7 Hz), 7.43 (m, 1H, J=2.9, 8.0 Hz), 7.22 (d, 1H, J=8.7 Hz), 6.9 (d, 1H, J=3.7 Hz); ESIMS: m/z 356 (M)+, 357 (M+H)+.

Example 8

5-nitro-2-thiophenecarbaldehyde 2-(6-trifluoromethyl-1,3-benzothiazol-2yl)hydrazone (3h)

The compound 3h was prepared according procedure described for 3a by employing 5-nitrothiophen aldehyde (157 mg, 1 mmol) and 2-hydrazino-6-trifluoromethyl-benzothiazole (233 mg, 1 mmol) at 70° C. for 2 h (yield 312 mg, 84%).

$^1$H NMR (DMSO-d$_6$, 200 MHz): δ 12.3 (bs, 1H), 7.84-7.82 (m, 2H, J=4.3 Hz), 7.60 (d, 1H), 7.43 (m, 1H, J=2.9, 8.0 Hz), 7.22 (d, 1H, J=8.7 Hz), 7.19 (d, 1H, J=4.38 Hz); ESIMS: m/z 372 (M+H)+.

Example 9

5-nitro-2-furaldehyde 2-(6-trifluoromethoxy-1,3-benzothiazol-2yl)hydrazone (3i)

The compound 3i was prepared according procedure described for 3a by employing 5-nitrofuran aldehyde (141 mg, 1 mmol) and 2-hydrazino-6-trifluoromethoxy-benzothiazole (249 mg, 1 mmol) at 70° C. for 2 h (yield 298 mg, 80%).

$^1$H NMR (DMSO-d$_6$, 200 MHz): δ 8.42 (bs, 1H), 7.44-7.41 (m, 2H), 7.36 (d, 1H), 7.27 (d, 1H, J=2.4 Hz), 7.30 (d, 1H, J=3.9 Hz), 7.14 (d, 1H, J=8.6 Hz), 6.48 (d, 1H, J=3.9 Hz); ESIMS: m/z 373 (M+H)+.

Example 10

5-nitro-2-thiophenecarbaldehyde 2-(6-trifluoromethoxy-1,3-benzothiazol-2yl)hydrazone (3j)

The compound 3j was prepared according procedure described for 3a by employing 5-nitrothiophen aldehyde (157 mg, 1 mmol) and 2-hydrazino-6-trifluoromethoxy-benzothiazole (249 mg, 1 mmol) at 70° C. for 2 h (yield 219 mg, 75%).

$^1$H NMR (DMSO-d$_6$, 200 MHz): δ 12.7 (bs, 1H), 8.14-8.10 (m, 2H, J=7.7, 4.3 Hz), 7.83 (m, 1H), 7.51 (d, 1H, J=4.5 Hz), 7.35-7.30 (m, 2H), 6.93 (dd, 1H, J=2.4, 8.7 Hz), 3.77 (s, 3H); ESIMS: m/z 388 (M+H)+.

Example 11

5-nitro-2-furaldehyde 2-(6-fluoro-1,3-benzothiazol-2yl)hydrazone (3k)

The compound 3k was prepared according procedure described for 3a by employing 5-nitrofuran aldehyde (157 mg, 1 mmol) and 2-hydrazino-6-fluoro-benzothiazole (183 mg, 1 mmol) at 70° C. for 2 h (yield 230 mg, 75%).

$^1$H NMR (DMSO-d$_6$, 200 MHz): δ 12.5 (bs, 1H), 7.86 (s, 1H), 7.57 (d, 1H, J=3.7 Hz), 7.39 (d, 1H, J=9.0 Hz), 7.28 (d, 1H, J=2.2 Hz), 7.02 (d, 1H, J=3.7 Hz), 6.86 (dd, 1H, J=9.0, 2.2 Hz); ESIMS: m/z 307 (M+H)+.

Example 12

5-nitro-2-thiophenecarbaldehyde 2-(6-chloro-1,3-benzothiazol-2yl)hydrazone (3n)

The compound 3n was prepared according procedure described for 3a by employing 5-nitrothiophen aldehyde (157 mg, 1 mmol) and 2-hydrazino-6-chloro-benzothiazole (199 mg, 1 mmol) at 70° C. for 2 h (yield 287 mg, 85%).

$^1$H NMR (DMSO-d$_6$, 200 MHz): δ 12.0 (bs, 1H), 7.84-7.82 (m, 2H, J=4.3 Hz), 7.60 (d, 1H), 7.43 (m, 1H, J=2.9, 8.0 Hz), 7.22 (d, 1H, J=8.7 Hz), 7.19 (d, 1H, J=4.3 Hz); ESIMS: m/z 338 (M)+.

Example 13

5-nitro-2-furaldehyde 2-(6-nitro-1,3-benzothiazol-2yl)hydrazone (3o)

The compound 3o was prepared according procedure described for 3a by employing 5-nitrofuran aldehyde (141 mg, 1 mmol) and 2-hydrazino-6-nitro-benzothiazole (210 mg, 1 mmol) at 70° C. for 2 h (yield 283 mg, 85%).

$^1$H NMR (DMSO-d$_6$, 200 MHz): δ 12.7 (bs, 1H), 8.10 (s, 1H), 7.71 (d, 1H, J=3.9 Hz), 7.43 (m, 1H), 7.30 (m, 1H, J=7.8 Hz), 7.15-7.12 (m, 2H, J=2.4, 6.8 Hz); ESIMS: m/z 333 (M)+.

Example 14

5-nitro-2-thiophenecarbaldehyde 2-(6-nitro-1,3-benzothiazol-2yl)hydrazone (3p)

The compound 3p was prepared according procedure described for 3a by employing 5-nitrothiophen aldehyde (157 mg, 1 mmol) and 2-hydrazino-6-nitro-benzothiazole (210 mg, 1 mmol) at 70° C. for 2 h (yield 303 mg, 87%).

$^1$H NMR (DMSO-$d_6$, 200 MHz): δ 12.0 (bs, 1H), 8.15-8.09 (m, 2H, J=4.7 Hz), 7.43 (m, 1H), 7.30 (m, 1H, J=7.8 Hz), 7.15-7.12 (m, 2H, J=2.4, 6.8 Hz); ESIMS: m/z 349 (M+H)$^+$.

General Procedure for Preparation of N-(6-halo/alkyl-1,3-benzothiazol-2yl)-5-nitro-2-furanecarbohydrazide (4a-h)

5-Nitro-2-furancarboxylic acidchloride (300 mg, 1 mmol) and 2-hydrazino-benzothiazole (1 mmol) in dry DMF (5 mL) were treated with triethylanine (3 mmol) followed by N,N-dimethylaminopyridine (DMAP) (730 mg, 2.5 mmol), and the resulting solution was stirred for 1 h at 0° C. and stirring continued at 25° C. for 11 h. Then pour the reaction into chloroform (70 mL), washed with washed with 10% NaHCO$_3$ (sodium bicarbonate) solution (2×20 mL). The organic phage was dried over Na$_2$SO$_4$ (sodium sulphate), concentrated in vacuum followed by column purification with ethyl acetate hexane system affords corresponding amides.

Example 15

N'2-(1,3-benzothiazol-2yl)-5-nitro-2-furanecarbohydrazide (4a)

The compound 4a was prepared according to above described method by using 5-nitro-2-furancarboxylic acid chloride (300 mg, 1 mmol) and 2-hydrazino-benzothiazole (300 mg, 1.5 mmol) which stirred for 1 h at 0° C. and stirring continued at 25° C. for 11 h (yield 245 mg, 85%).

$^1$H NMR (DMSO-$d_6$, 200 MHz): δ 13.7 (bs, 1H), 9.0 (bs, 1H), 8.42-8.40 (m, 1H), 8.20 (m, 1H), 7.88-7.82 (m, 2H), 7.73-7.68 (m, 2H); ESIMS: m/z 304 (M)$^+$.

Example 16

N'2-(6-methyl-1,3-benzothiazol-2yl)-5-nitro-2-furanecarbohydrazide (4b)

The compound 4b was prepared according to above described method by using 5-nitro-2-furancarboxylic acid chloride (300 mg, 1 mmol) and 2-hydrazino-6-methylbenzothiazole (179 mg, 1 mmol) which stirred for 1 h at 0° C. and stirring continued at 25° C. for 11 h (yield 216 mg, 85%).

$^1$H NMR (DMSO-$d_6$, 200 MHz): δ 11.0 (bs, 1H), 8.02 (bs, 1H), 7.76 (d, 1H, J=3.9 Hz), 7.45 (m, 1H), 7.37 (d, 1H, J=8.1 Hz), 7.12 (d, 1H, J=3.7 Hz), 6.98 (dd, 1H, J=2.4, 8.6 Hz), 2.47 (s, 3H); ESIMS: m/z 319 (M+H)$^+$.

Example 17

N'2-(6-methoxy-1,3-benzothiazol-2yl)-5-nitro-2-furanecarbohydrazide (4c)

The compound 4c was prepared according to above described method by using 5-nitro-2-furancarboxylic acid chloride (300 mg, 1 mmol) and 2-hydrazino-6-methoxybenzothiazole (260 mg, 1 mmol) which stirred for 1 h at 0° C. and stirring continued at 25° C. for 11 h (yield 283 mg, 85%).

$^1$H NMR (DMSO-$d_6$, 200 MHz): δ 12.0 (bs, 1H), 8.02 (bs, 1H), 7.76 (d, 1H, J=3.9 Hz), 7.45 (m, 1H), 7.40 (d, 1H, J=8.1 Hz), 7.12 (d, 1H, J=3.7 Hz), 6.93 (dd, 1H, J=2.4, 8.6 Hz), 3.77 (s, 3H); ESIMS: m/z 334 (M)$^+$.

Example 18

N'2-(6-trifluoromethyl-1,3-benzothiazol-2yl)-5-nitro-2-furanecarbohydrazide (4d)

The compound 8c was prepared according to above described method by using 5-nitro-2-furancarboxylic acid chloride (300 mg, 1 mmol) and 2-hydrazino-6-trifluoromethylbenzothiazole (419 mg, 1 mmol) which stirred for 1 h at 0° C. and stirring continued at 25° C. for 11 h (yield 279 mg, 75%).

$^1$H NMR (DMSO-$d_6$, 200 MHz): δ 11.3 (bs, 1H), 9.94 (bs, 1H), 7.80 (d, 1H, J=3.9 Hz), 7.55 (m, 1H, J=7.8 Hz), 7.38 (m, 1H, J=7.8 Hz), 6.88 (dd, 1H, J=9.1, 2.6 Hz), 6.81 (d, 1H, J=3.9 Hz); ESIMS: m/z 373 (M+H)$^+$.

Example 19

N'2-(6-trifluoromethoxy-1,3-benzothiazol-2yl)-5-nitro-2-furanecarbohydrazide (4e)

The compound 4e was prepared according to above described method by using 5-nitro-2-furancarboxylic acid chloride (430 mg, 1 mmol) and 2-hydrazino-6-trifluoromethoxybenzothiazole (319 mg, 1.5 mmol) which stirred for 1 h at 0° C. and stirring continued at 25° C. for 11 h (yield 287 mg, 87%).

$^1$H NMR (DMSO-$d_6$, 200 MHz): δ 12.5 (bs, 1H), 8.2 (bs, 1H), 7.9 (d, 1H), 7.7 (d, 1H, J=3.9 Hz), 7.54 (m, 1H), 7.50 (d, 1H, J=8.1 Hz), 7.12 (d, 1H, J=3.7 Hz); ESIMS: m/z 388 (M)$^+$.

Example 20

N'2-(6-fluoromethoxy-1,3-benzothiazol-2yl)-5-nitro-2-furanecarbohydrazide (4f)

The compound 4f was prepared according to above described method by using 5-nitro-2-furancarboxylic acid chloride (430 mg, 1 mmol) and 2-hydrazino-6-fluoromethoxybenzothiazole (274 mg, 1.5 mmol) which stirred for 1 h at 0° C. and stirring continued at 25° C. for 11 h (yield 242 mg, 75%).

$^1$H NMR (DMSO-$d_6$, 200 MHz): δ 11.4 (bs, 1H), 8.18 (bs, 1H), 7.84 (d, 1H), 7.73 (d, 1H, J=3.9 Hz), 7.48 (m, 1H), 7.40 (d, 1H, J=8.1 Hz), 7.10 (d, 1H, J=3.7 Hz); ESIMS: m/z 323 (M+H)$^+$.

Example 21

N'2-(6-chloromethoxy-1,3-benzothiazol-2yl)-5-nitro-2-furanecarbohydrazide (4g)

The compound 4g was prepared according to above described method by using 5-nitro-2-furancarboxylic acid chloride (430 mg, 1 mmol) and 2-hydrazino-6-chloromethoxybenzothiazole (298 mg, 1.5 mmol) which stirred for 1 h at 0° C. and stirring continued at 25° C. for 11 h (yield 237 mg, 70%).

¹H NMR (DMSO-d₆, 200 MHz): δ 11.3 (bs, 1H), 8.14 (bs, 1H), 7.82 (d, 1H), 7.71 (d, 1H, J=3.9 Hz), 7.44 (m, 1H), 7.39 (d, 1H, J=8.1 Hz), 7.10 (d, 1H, J=3.7 Hz); ESIMS: m/z 339 (M+H)⁺.

Example 22

N'2-(6-Nitro-1,3-benzothiazol-2yl)-5-nitro-2-furanecarbohydrazide (4h)

The compound 4h was prepared according to above described method by using 5-nitro-2-furancarboxylic acid chloride (430 mg, 1.5 mmol) and 2-hydrazino-6-nitrobenzothiazole (290 mg, 1 mmol) which stirred for 1 h at 0° C. and stirring continued at 25° C. for 11 h (yield 283 mg, 87%).
¹H NMR (DMSO-d₆, 200 MHz): δ 8.2 (bs, 1H), 8.0 (d, 1H), 7.9 (m, 1H), 7.76 (d, 1H, J=3.9 Hz), 7.45 (d, 1H, J=8.0 Hz), 7.12 (d, 1H, J=3.7 Hz); ESIMS: m/z 244 (M)⁺.

Example 23

N2-[2-(benzoylamino)-1,3-benzothiazol-6yl]-5-nitrofuramide (6a)

Benzoylchloride (140 mg, 1 mmol) and 2-amino-6-nitrobenzothiazole (1h) (195 mg, 1 mmol) in dry DMF (5 mL) were treated with triethylanine (0.418 mL, 3 mmol) followed by N,N-dimethylaminopyridine (DMAP) (305 mg, 2.5 mmol), and the resulting solution was stirred was stirred for 1 h at 0° C. and stirring continued at 25° C. for 11 h. Then the reaction mixture poured on to crushed ice and stirred well, formed precipitate filtered and washed with cold dichloromethane (20 mL), washed with 10% NaHCO₃ solution (2×20 mL). The solid was recrystallization by using THF affording compound 5a as a yellow solid (Yield: 174 mg, 55%)
To a solution of (5a) (300 mg, 1 mmol) in THF (10 ml), ammonium formate (130 mg, 2 mmol) was added and zinc dust (15 mg, 0.2 mmol) was added and stirred for 30 minutes at room temperature. After the completion of reaction as indicated by TLC, the solvent was removed under reduced pressure, neutralized with saturated sodium bicarbonate solution and extracted with chloroform. The solvent was removed under reduced pressure to give the desired amino intermediate. This was directly used for the further step.
To a solution of 5-nitro-2-furoicacid (157 mg, 1 mmol) and triethylamine (0.25 mL, 2 mmol) in dry DMF (5 mL), 1-Ethyl-3-(3-Dimethylaminopropyl)carbodiimide (EDC) (155 mg, 1 mmol) and 1-hydroxy-1,2,3-benzotriazole (HoBt) (135 mg, 1 mmol) were added. After five minutes, previously prepared amine (215 mg, 0.8 mmol) was added to the reaction mixture and stirred at room temperature (25° C.) for 12 hrs. After the completion of reaction as indicated by TLC, ice cold water (15 mL) was added to the reaction mixture, filtered the precipitate and gave wash with cold THF to give the desired product (6a). Yield 204 mg, 50%; ¹H NMR (DMSO-d₆) δ 12.45 (bs, 1H, —NH), 10.52 (bs, 1H, —NH), 8.37 (s, 1H), 8.16 (d, 2H), 7.78 (dd, 1H), 7.67 (d, 1H), 7.60 (d, 1H), 7.57 (d, 1H), 7.55 (d, 1H), 7.49 (t, 2H); MS (ESI) m/z 409 (M+H)⁺.

Example 24

N2-{2-[(4-fluorobenzoyl)amino]-1,3-benzothiazol-6yl}-5-nitrofuramide (6f)

The compound 6f was prepared according to the above described method using compound 5f (317 mg, 1 mmol) and 5-nitro-2-furoicacid (157 mg, 1 mmol). Yield 235 mg, 55%; ¹H NMR (DMSO-d₆) δ 12.4 (bs, 1H, —NH), 10.5 (bs, 1H, —NH), 8.37 (s, 1H), 8.18 (d, 2H), 7.78 (d, 1H), 7.69 (d, 1H), 7.57 (d, 1H), 7.55 (d, 1H), 7.35 (d, 2H); MS (ESI) m/z 427 (M+H)⁺.

Example 25

N2-{2-[(4-chlorobenzoyl)amino]-1,3-benzothiazol-6yl}-5-nitrofuramide (6g)

The compound 6g was prepared according to the above described method using compound 5g (333 mg, 1 mmol) and 5-nitro-2-furoicacid (157 mg, 1 mmol). Yield 221 mg, 50%; ¹H NMR (DMSO-d₆) δ 11.4 (bs, 1H, —NH), 9.51 (bs, 1H, —NH), 8.37 (s, 1H), 7.92 (d, 2H), 7.78 (d, 1H), 7.69 (d, 1H), 7.57 (d, 1H), 7.55 (d, 1H), 7.48 (d, 2H); MS (ESI) m/z 443 (M+H)⁺.

Example 26

N2-{2-[(2,4-difluorobenzoyl)amino]-1,3-benzothiazol-6yl}-5-nitrofuramide (6i)

The compound 6i was prepared according to the above described method using compound 5i (335 mg, 1 mmol) and 5-nitro-2-furoicacid (157 mg, 1 mmol). Yield 244 mg, 55%; ¹H NMR (DMSO-d₆) δ 10.4 (bs, 1H, —NH), 9.51 (bs, 1H, —NH), 8.37 (s, 1H), 7.99-7.97 (m, 1H), 7.78 (d, 1H), 7.69 (d, 1H), 7.57 (d, 1H), 7.55 (d, 1H), 7.20 (m, 1H), 6.85 (s, 1H); MS (ESI) m/z 445 (M+H)⁺.

Example 27

N4-(6-{[(5-nitrofuryl)carbonyl]amino}-1,3-benzothiazol-2-yl)isonicotinamide (6n)

The compound 6n was prepared according to the above described method using compound 5n (300 mg, 1 mmol) and 5-nitro-2-furoicacid (157 mg, 1 mmol). Yield 220 mg, 54%; ¹H NMR (DMSO-d₆) δ 11.4 (bs, 1H, —NH), 9.51 (bs, 1H, —NH), 8.73-8.71 (m, 2H), 8.37 (s, 1H), 7.84-7.83 (m, 2H), 7.78 (d, 1H), 7.69 (d, 1H), 7.57 (d, 1H), 7.55 (d, 1H); MS (ESI) m/z 410 (M+H)⁺.

Example 28

N3-(6-{[(5-nitrofuryl)carbonyl]amino}-1,3-benzothiazol-2-yl)nicotinamide (6o)

The compound 6O was prepared according to the above described method using compound 5O (300 mg, 1 mmol) and 5-nitro-2-furoicacid (157 mg, 1 mmol). Yield 220 mg, 54%; ¹H NMR (DMSO-d₆) δ 11.4 (bs, 1H, —NH), 9.51 (bs, 1H, —NH), 9.10-9.08 (m, 1H), 8.37 (s, 1H), 8.67-8.66 (m, 1H), 8.41-8.38 (m, 1H), 7.78 (d, 1H), 7.69 (d, 1H), 7.65-7.64 (m, 1H), 7.57 (d, 1H), 7.55 (d, 1H); MS (ESI) m/z 410 (M+H)⁺.

Example 29

N2-(6-{[(5-nitrofuryl)carbonyl]amino}-1,3-benzothiazol-2-yl)pyrazinecarboxamide (6p)

The compound 6p was prepared according to the above described method using compound 5p (301 mg, 1 mmol) and 5-nitro-2-furoicacid (157 mg, 1 mmol). Yield 266 mg, 65%; ¹H NMR (DMSO-d₆) δ 12.0 (bs, 1H, —NH), 10.9 (bs, 1H, —NH), 8.95 (s, 1H), 8.68 (d, 1H), 8.48 (d, 1H), 8.35 (s, 1H), 7.80 (d, 1H), 7.71 (d, 1H), 7.65 (d, 1H), 7.51 (d, 1H); MS (ESI) m/z 411 (M+H)+.

Example 30

N2-(2-{[(E)-3-(4-fluorophenyl)-2-propenoyl]amino}-1,3-benzothiazol-6-yl)-5-nitro-2-furamide (6v)

The compound 6v was prepared according to the above described method using compound 5v (343 mg, 1 mmol) and 5-nitro-2-furoicacid (157 mg, 1 mmol). Yield 235 mg, 54%; $^1$H NMR (DMSO-$d_6$) δ 11.4 (bs, 1H, —NH), 9.51 (bs, 1H, —NH), 8.73-8.71 (m, 2H), 8.51 (d, 1H), 8.37 (s, 1H), 7.78 (d, 1H), 7.69 (d, 1H), 7.57 (d, 1H), 7.55 (d, 1H), 7.45-7.43 (m, 2H), 6.52 (d, 1H); MS (ESI) m/z 453 (M+H)+.

Example 31

Synthesis of N2-(2-{[(5-nitro-2-furyl)carbonyl]amino}-1,3-benzothiazol-6-yl)-5-nitro-2-furamide (8a)

5-Nitro-2-furancarboxylic acid (300 mg, 2 mmol) and 2,6-diaminobenzothiazole (7) (165 mg, 1 mmol) in dry DMF (5 mL) were treated with 1-[3-(dimethylamino)propyl]-3-ethylcarbodiimide hydrochloride (EDCI) 98% (310 mg, 2 mmol) followed by N,N-dimethylaminopyridine (DMAP) (305 mg, 2.5 mmol), and the resulting solution was stirred for 14 h at room temperature. Then the reaction mixture poured on to crushed ice and stirred well, formed precipitate filtered and washed with cold dichloromethane (20 mL), washed with 10% $NaHCO_3$ solution (2×20 mL), followed by recrystalyzed from methanol affords pure compound (8a). Yield 287 mg, 65%.

$^1$H NMR (DMSO-$d_6$, 200 MHz): δ 8.02 (bs, 1H), 7.80 (d, 2H, J=3.9 Mz), 7.7 (m, 1H), 7.60 (d, 2H, J=8.1 Hz), 7.65 (d, 2H, J=3.7 Hz); ESIMS: m/z 443 (M)+.

Example 32

N2-(2-{[(1-methyl-4-nitro-1H-2-pyrrolyl)carbonyl]amino}-1,3-benzothiazol-6-yl)-1-methyl-4-nitro-1H-2-pyrrolcarboxamide (8b)

The compound 8b was prepared according to the above described method using compound 7 (165 mg, 1 mmol) and 1-methyl-4-nitro-1H-pyrrole-2-carboxylic acid (340 mg, 2 mmol). Yield 290 mg, 60%; $^1$H NMR (DMSO-$d_6$) δ 10.9 (bs, 1H, —NH), 8.54 (s, 1H), 7.95 (s, 2H), 7.74-7.71 (m, 2H), 7.50 (s, 2H), 3.96 (s, 6H); ESIMS: m/z 470 (M+H)+.

Example 33

N2-(2-{[(1-methyl-5-nitro-1H-2-imadazolyl)carbonyl]amino}-1,3-benzothiazol-6-yl)-1-methyl-5-nitro-1H-2-imadazolecarboxamide (8c)

The compound 8c was prepared according to the above described method using compound 7 (165 mg, 1 mmol) and 1-methyl-5-nitro-1H-imidazole-2-carboxylic acid (342 mg, 2 mmol). Yield 300 mg, 63%; $^1$H NMR (DMSO-$d_6$) δ 9.51 (bs, 1H, —NH), 8.54 (s, 1H), 8.20 (s, 2H), 7.74-7.71 (m, 2H), 3.76 (s, 6H); ESIMS: m/z 472 (M+H)+.

Example 34

N2-(2-{[(1-methyl-3-nitro-1H-2-pyrazolyl)carbonyl]amino}-1,3-benzothiazol-6-yl)-1-methyl-3-nitro-1H-2-pyrazolecarboxamide (8d)

The compound 8d was prepared according to the above described method using compound 7 (165 mg, 1 mmol) and 1-methyl-3-nitro-1H-pyrazole-5-carboxylic acid (342 mg, 2 mmol). Yield 258 mg, 55%; $^1$H NMR (DMSO-$d_6$) δ 9.51 (bs, 1H, —NH), 8.54 (s, 1H), 7.74-7.71 (m, 2H), 6.50 (s, 2H), 3.96 (s, 6H); ESIMS: m/z 472 (M+H)+.

Biological Data

1. Antimycobacterial Activity

The compounds 3a-f, 4a-h, 6a,f,g,i,o,p,q,w, and 8a have been evaluated or the antimycobacterial activity and the results are summarized in Table 1. All compounds were initially screened against M. tuberculosis $H_{37}$Rv at the single concentration of 16 (μg/mL). The active compounds from this screening were further tested for Minimum Inhibitory Concentration (MIC) determination using a broth microdilution assay. Compounds demonstrating at least 90% inhibition in the primary screen were retested at lower concentrations by serial dilution against M. tuberculosis $H_{37}$Rv to determine the actual MIC, using the Nitrate Reductase Assay (NRA). The growth in the microtitre plate is indicated by the change in color to pink detected by the addition of NRA reagent. The MIC is defined as the lowest concentration of the compound showing no change in the color relative to controls. Rifampicin and Isoniazid were used as reference drugs. All these compounds have shown activity between 0.5→16 μg/mL. Among these compounds nitrofurane derived benzothiazoles (3j, 4e, 6a, 6f, 6g, 6i, 6p, 6w and 8a) have shown good in vivo anti-mycobacterial activity (0.5-8 μg/mL).

TABLE 1

Antimycobacterial activity of compounds 3a-f, 4, 6a, f, g, i, o, p, q, w, and 8a against M. tuberculosis H37Rv (MIC in μg/mL).

| Comp | MIC (μg/mL) | C log P$^c$ | CMR$^d$ | M. Wt | Mol. For |
|---|---|---|---|---|---|
| 3a | >16 | 3.24 | 7.63 | 288.28 | $C_{12}H_8N_4O_3S$ |
| 3b | >16 | 3.78 | 8.23 | 304.01 | $C_{12}H_8N_4O_2S_2$ |
| 3c | >16 | 3.74 | 8.10 | 302.04 | $C_{13}H_{10}N_4O_3S$ |
| 3d | >16 | 4.28 | 8.69 | 318.37 | $C_{13}H_{10}N_4O_2S_2$ |
| 3e | >16 | 3.54 | 8.25 | 318.31 | $C_{13}H_{10}N_4O_4S$ |
| 3f | >16 | 4.07 | 8.85 | 334.37 | $C_{13}H_{10}N_4O_3S_2$ |
| 3g | >16 | 4.19 | 8.14 | 356.28 | $C_{13}H_7F_3N_4O_3S$ |
| 3h | >16 | 4.72 | 8.74 | 372.35 | $C_{13}H_7F_3N_4O_2S_2$ |
| 3i | >16 | 4.65 | 8.30 | 372.28 | $C_{13}H_7F_3N_4O_4S$ |
| 3j | 1 | 5.18 | 8.89 | 388.34 | $C_{13}H_7F_3N_4O_3S_2$ |
| 3k | >16 | 3.38 | 7.65 | 306.27 | $C_{12}H_7FN_4O_3S$ |
| 3l | >16 | 3.91 | 8.24 | 322.34 | $C_{12}H_7FN_4O_2S_2$ |
| 3m | 16 | 3.95 | 8.13 | 322.73 | $C_{12}H_7ClN_4O_3S$ |
| 3n | >16 | 4.48 | 8.72 | 338.79 | $C_{12}H_7ClN_4O_2S_2$ |
| 3o | 16 | 3.09 | 8.26 | 333.28 | $C_{12}H_7N_5O_5S$ |
| 3p | >16 | 3.62 | 8.84 | 349.35 | $C_{12}H_7N_5O_4S_2$ |
| 4a | >16 | 1.41 | 7.54 | 304.28 | $C_{12}H_8N_4O_4S$ |
| 4b | >16 | 1.91 | 8.01 | 318.03 | $C_{13}H_{10}N_4O_4S$ |
| 4c | >16 | 1.70 | 8.16 | 334.31 | $C_{13}H_{10}N_4O_5S$ |
| 4d | >16 | 2.32 | 8.05 | 372.28 | $C_{13}H_7F_3N_4O_4S$ |
| 4e | 2 | 2.81 | 8.21 | 388.28 | $C_{13}H_7F_3N_4O_5S$ |
| 4f | >16 | 1.55 | 7.56 | 322.27 | $C_{12}H_7FN_4O_4S$ |
| 4g | >16 | 2.12 | 8.03 | 337.98 | $C_{12}H_7ClN_4O_4S$ |
| 4h | 16 | 1.21 | 8.15 | 349.09 | $C_{12}H_7N_5O_8S$ |
| 6a | 1 | 3.69 | 10.55 | 408.05 | $C_{19}H_{12}N_4O_5S$ |
| 6f | 0.5 | 4.89 | 11.2 | 492.03 | $C_{20}H_{11}F_3N_4O_6S$ |
| 6g | 0.5 | 3.86 | 10.57 | 426.04 | $C_{19}H_{11}FN_4O_5S$ |
| 6i | 0.5 | 3.47 | 11.66 | 472.02 | $C_{20}H_{13}ClN_4O_6S$ |
| 6o | 4.0 | 3.73 | 11.15 | 452.39 | $C_{20}H_{12}N_4O_7S$ |
| 6p | 1 | 2.48 | 10.3 | 409.04 | $C_{18}H_{11}N_5O_5S$ |
| 6q | 8.0 | 2.83 | 10.34 | 409.04 | $C_{18}H_{11}N_5O_5S$ |

TABLE 1-continued

Antimycobacterial activity of compounds 3a-f, 4, 6a, f, g, i, o, p, q, w, and 8a against M. tuberculosis H37Rv (MIC in µg/mL).

| Comp | MIC (µg/mL) | C log P[c] | CMR[d] | M. Wt | Mol. For |
|---|---|---|---|---|---|
| 6w | 2.0 | 5.59 | 12.27 | 502.42 | $C_{22}H_{13}F_3N_4O_5S$ |
| 8a | 2 | 2.72 | 10.38 | 443.35 | $C_{17}H_9N_5O_8S$ |
| RMP[a] | 0.25 | | | | |
| INH[b] | 0.5 | | | | |

[a]Rifampcin,
[b]Isoniazid;
[c]C log P (Hydrophobicity); and
[d]CMR (molar refractivity) was calculated using the Chem Draw Ultra, version 9.0

2. Cytotoxicity Assay

The potent compounds 3j, 4e, 6a, 6f, 6g, 6i, and 6p were evaluated for cytotoxic effect on AML-12 cell lines using MTT assay, in a 96 well plate format. Cells were incubated in Dulbecco's Modified Eagle's Medium (DMEM) containing 10% fetal calf serum (FCS) with the test material (2-100 µg/ml) for 24 hrs at 37° C. in $CO_2$ incubator. After the completion of incubation 3-(4,5-dimethylthiazol-2-yl)-2,5-diphenyltetrazolium bromide (MTT) was added and cells were further incubated for 3 h at 37° C. in $CO_2$ incubator. Formation of formazan salt by mitochondrial dehydrogenases, and was determined by Elisa reader at 565 nm (Multiskan Spectrum; Thermo Electron Corporation, USA). The percentage cytotoxicity was calculated with respect to the untreated cells. The results were summarized in Table 2.

TABLE 2

Cytotoxicity assay on cell line AML-12 (µg/mL)

| Compound code | Cytotoxicity |
|---|---|
| 3j | >100 |
| 4e | >100 |
| 6a | >100 |
| 6f | >100 |
| 6g | >100 |
| 6i | >100 |
| 6o | >100 |
| 6p | >100 |
| 6q | >100 |
| 6w | >100 |

3. In Vivo Efficacy Studies

The Compounds 3j, 4e, 6a, 6f, 6g, 6i, 6p, 6w and 8a demonstrated good in vitro activity against M. tuberculosis isolates and drug resistance strains. The active compounds of the series has been subjected to cytotoxicity assay (MTT assay), the tested compounds does not show any pathological effects. Subsequently, compounds 6f, 6g and 6i were tested for in vivo efficacy against M. tuberculosis at a dose of 25 mg/kg (Table 3) in six week-old female Swiss albino mice. In this model the mice were infected through intra nasally with 25 µL volume containing $1.5 \times 10^6$ CFU/mouse of viable M. tuberculosis (H37Rv). Drug treatment began after inoculation of the animal with microorganism and continued for 10 days by intraperitoneal route. After 35 days of post-infection, the left lungs was aseptically removed and ground in a tissue homogenizer, and the number of viable organisms was determined by serial 10-fold dilutions and subsequent inoculation onto 7H10 agar plates. Cultures were incubated at 37° C. in ambient air for 4 weeks prior to counting. Bacterial counts were measured and compared with the counts from negative (untreated) controls (Mean culture forming units (CFU) in lung: 6.3±0.22). Compound 6f, 6g and 6i dose exhibited bacteriostatic activities and maintained the CFU load as the early control and decreased the bacterial load in lung 1.0 protections with late control, respectively, and was considered to be promising in reducing bacterial count in lung tissues.

TABLE 3

In vivo efficacy studies of compounds 6f, 6g and 6i against M. tuberculosis in lungs of infected Mice.

| S. No | N[b] | Treatment groupa | Log10 CFU/left Lung |
|---|---|---|---|
| 1 | 8 | Early Control | 6.0 ± 0.25 |
| 2 | 7c | Late Control | 7.3 ± 0.37 |
| 3 | 7c | Rifampcin (20 mg/kg) | 2.0 ± 0.41 |
| 4 | 7c | Comp. (6f) 25 (mg/kg) | 6.0 ± 0.13 |
| 5 | 7c | Comp. (6g) 25 (mg/kg) | 6.1 ± 0.48 |
| 6 | 7c | Comp (6i) 25 (mg/kg) | 6.3 ± 0.37 | aTreatment was started 1 week after mice received ≈ 1 × 106 viable mycobacteria intranasal. The drugs were evaluated at the following doses: RIF, 20 mg/kg; 6f, 6g, 6i, 25 mg/kg for 4 weeks (PO x OD),
bNumber of mice per group,
cOne mouse found dead during therapy.

TABLE 4

Comparative antimycobacterial activity data of benzothiazole conjugates against M. tuberculosis H37Rv (MIC in µg/mL) with closest benzothiazole compounds.

| Compound code | MIC (µg/mL) |
|---|---|
| 3j | 1 |
| 6a | 1 |
| 6f | 0.5 |
| 6g | 0.5 |
| 6i | 0.5 |
| 6p | 1 |
| | 1.9 |

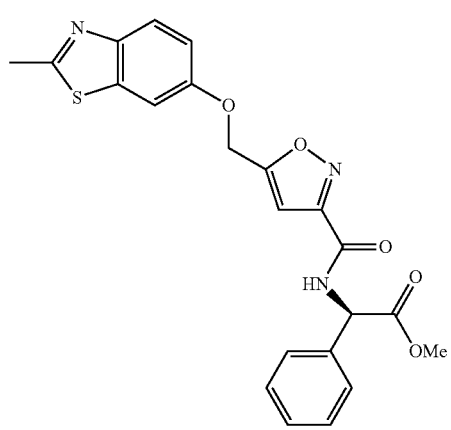 [SMILES: COC(=O)[C@H](NC(=O)c1cc(COc2ccc3nc(C)sc3c2)on1)c1ccccc1]

TABLE 4-continued

Comparative antimycobacterial activity data of benzothiazole conjugates against *M. tuberculosis* H37Rv (MIC in µg/mL) with closest benzothiazole compounds.

| Compound code | MIC (µg/mL) |
|---|---|
| (structure) | 1.4 |
| (structure) | >6.5 |
| (structure) | 2 |
| (structure) | 2 |
| (structure) | 73 |

Advantages of Present Disclosure

1. The present disclosure provides benzothiazole derivatives of general formula A useful as anti-tubercular chemotherapeutic agents.
2. It also provides a process for the preparation of benzothiazole derivatives of general formula A.

What is claimed is:

1. A benzothiazole compound selected from the group consisting of formula 3a-p, 4a-h, 6a-t and 8a-d set forth below:

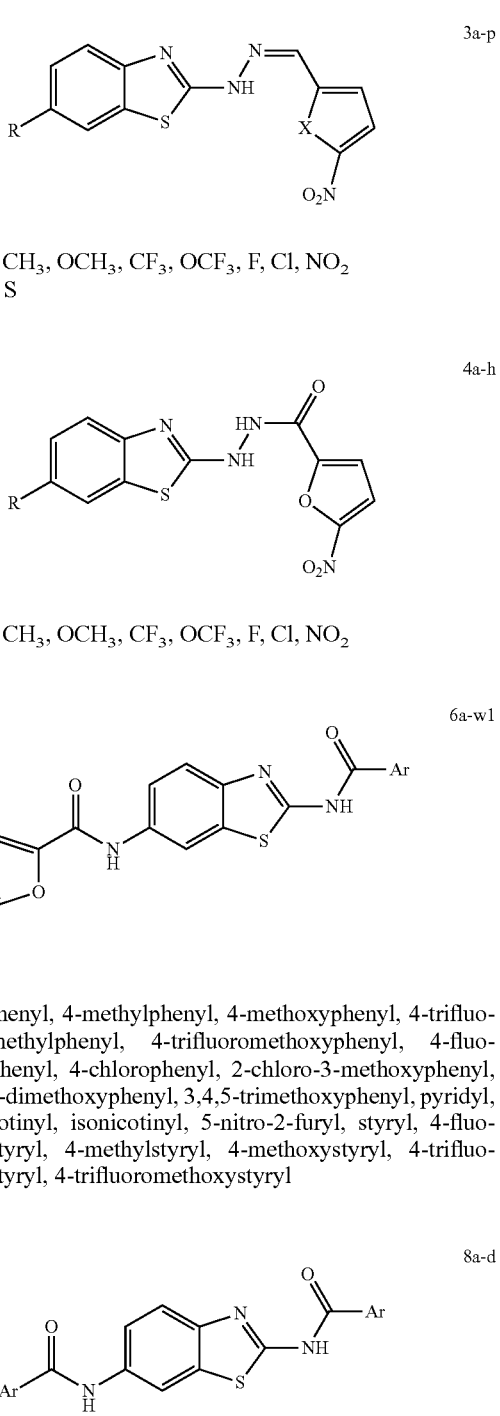

R=H, CH$_3$, OCH$_3$, CF$_3$, OCF$_3$, F, Cl, NO$_2$
X=O, S

R=H, CH$_3$, OCH$_3$, CF$_3$, OCF$_3$, F, Cl, NO$_2$

Ar=Phenyl, 4-methylphenyl, 4-methoxyphenyl, 4-trifluoromethylphenyl, 4-trifluoromethoxyphenyl, 4-fluorophenyl, 4-chlorophenyl, 2-chloro-3-methoxyphenyl, 3,5-dimethoxyphenyl, 3,4,5-trimethoxyphenyl, pyridyl, nicotinyl, isonicotinyl, 5-nitro-2-furyl, styryl, 4-fluorostyryl, 4-methylstyryl, 4-methoxystyryl, 4-trifluorostyryl, 4-trifluoromethoxystyryl Ar=5-nitro-2-furyl, 1-methyl-4-nitro-1H-2-pyrrolyl, 1-methyl-5-nitro-1H-2-imidazolyl, 1-methyl-3-nitro-1H-2-pyrazolyl.

2. The benzothiazole compound as claimed in claim 1 wherein the structural formula of the representative compounds are:
   3a) 5-nitro-2-furaldehyde 2-(1,3-benzothiazole-2-yl)hydrazone;
   3b) 5-nitro-2-thiophenecarbaldehyde 2-(1,3-benzothiazole-2-yl)hydrazone;
   3c) 5-nitro-2-furaldehyde 2-(6-methyl-1,3-benzothiazole-2-yl)hydrazone;

3d) 5-nitro-2-thiophenecarbaldehyde 2-(6-methyl-1,3-benzothiazole-2-yl)hydrazone;
3e) 5-nitro-2-furaldehyde 2-(6-methoxy-1,3-benzothiazole-2-yl)hydrazone;
3f) 5-nitro-2-thiophenecarbaldehyde 2-(6-methoxy-1,3-benzothiazole-2-yl)hydrazone;
3g) 5-nitro-2-furaldehyde 2-(6-trifluoromethyl-1,3-benzothiazole-2-yl)hydrazone;
3h) 5-nitro-2-thiophenecarbaldehyde 2-(6-trifluoromethyl-1,3-benzothiazole-2-yl)hydrazone;
3i) 5-nitro-2-furaldehyde 2-(6-trifluoromethoxy-1,3-benzothiazole-2-yl)hydrazone;
3j) 5-nitro-2-thiophenecarbaldehyde 2-(6-trifluoromethoxy-1,3-benzothiazole-2-yl)hydrazone;
3k) 5-nitro-2-furaldehyde 2-(6-fluoro-1,3-benzothiazole-2-yl)hydrazone;
3l) 5-nitro-2-thiophenecarbaldehyde 2-(6-fluoro-1,3-benzothiazole-2-yl)hydrazone;
3m) 5-nitro-2-furaldehyde 2-(6-chloro-1,3-benzothiazole-2-yl)hydrazone;
3n) 5-nitro-2-thiophenecarbaldehyde 2-(6-chloro-1,3-benzothiazole-2-yl)hydrazone;
3o) 5-nitro-2-furaldehyde 2-(6-nitro-1,3-benzothiazole-2-yl)hydrazone;
3p) 5-nitro-2-thiophenecarbaldehyde 2-(6-nitro-1,3-benzothiazole-2-yl)hydrazone;
4a) N'2-(1,3-benzothiazol-2-yl)-5-nitro-2-furancarbohydrazide;
4b) N'2-(6-methyl-1,3-benzothiazol-2yl)-5-nitro-2-furancarbohydrazide;
4c) N'2-(6-methoxy-1,3-benzothiazol-2-yl)-5-nitro-2-furancarbohydrazide;
4d) N'2-(6-trifluoromethyl-1,3-benzothiazol-2-yl)-5-nitro-2-furancarbohydrazide;
4e) N'2-(6-trifluoromethoxy-1,3-benzothiazol-2-yl)-5-nitro-2-furanecarbohydrazide;
4f) N'2-(6-fluoro-1,3-benzothiazol-2-yl)-5-nitro-2-furanecarbohydrazide;
4g) N'2-(6-chloro-1,3-benzothiazol-2-yl)-5-nitro-2-furanecarbohydrazide;
4h) N'2-(6-nitro-1,3-benzothiazol-2-yl)-5-nitro-2-furanecarbohydrazide;
6a) N2-[2-(benzoylamino)-1,3-benzothiazol-6-yl]-5-nitrofuramide;
6b) N2-{2-[(4-methylbenzoyl)amino]-1,3-benzothiazol-6-yl}-5-nitrofuramide;
6c) N2-{2-[(4-methoxybenzoyl)amino]-1,3-benzothiazol-6-yl}-5-nitrofuramide;
6d) N2-{2-[(4-trifluoromethylbenzoyl)amino]-1,3-benzothiazol-6-yl}-5-nitrofuramide;
6e) N2-{2-[(4-trifluoromethoxybenzoyl)amino]-1,3-benzothiazol-6-yl}-5-nitrofuramide;
6f) N2-{2-[(4-fluorobenzoyl)amino]-1,3-benzothiazol-6-yl}-5-nitrofuramide;
6g) N2-{2-[(4-chlorobenzoyl)amino]-1,3-benzothiazol-6-yl}-5-nitrofuramide;
6h) N2-{2-[(2-chloro-3-methoxybenzoyl)amino]-1,3-benzothiazol-6-yl}-5-nitrofuramide;
6i) N2-{2-[(3,5-dimethoxybenzoyl)amino]-1,3-benzothiazol-6-yl}-5-nitrofuramide;
6j) N2-{2-[(3,4,5-trimethoxybenzoyl)amino]-1,3-benzothiazol-6-yl}-5-nitrofuramide;
6k) N5-(6-{[(5-nitro-2-furyl)carbonyl]amino}-1,3-benzothiazol-2-yl)-1,3-benzodioxole-5-carboxamide;
6l) N4-(6-{[(5-nitro-2-furyl)carbonyl]amino}-1,3-benzothiazol-2-yl)isonicotinamide;
6m) N3-(6-{[(5-nitro-2-furyl)carbonyl]amino}-1,3-benzothiazol-2-yl)nicotinamide;
6n) N2-(2-{[(E)-3-phenyl-2-propenoyl]amino}-1,3-benzothiazol-6-yl)-5-nitro-2-furamide;
6o) N2-(2-{[(E)-3-(4-methylphenyl)-2-propenoyl]amino}-1,3-benzothiazol-6-yl)-5-nitro-2-furamide;
6p) N2-(2-{[(E)-3-(4-methoxyphenyl)-2-propenoyl]amino}-1,3-benzothiazol-6-yl)-5-nitro-2-furamide;
6q) N2-(2-{[(E)-3-(4-trifluoromethylphenyl)-2-propenoyl]amino}-1,3-benzothiazol-6-yl)-5-nitro-2-furamide;
6r) N2-(2-{[(E)-3-(4-trifluoromethoxyphenyl)-2-propenoyl]amino}-1,3-benzothiazol-6-yl)-5-nitro-2-furamide;
6s) N2-(2-{[(E)-3-(4-fluorophenyl)-2-propenoyl]amino}-1,3-benzothiazol-6-yl)-5-nitro-2-furamide;
6t) N2-(2-{[(E)-3-(4-chlorophenyl)-2-propenoyl]amino}-1,3-benzothiazol-6-yl)-5-nitro-2-furamide;
8a) N2-(2-{[(5-nitro-2-furyl)carbonyl]amino}-1,3-benzothiazol-6-yl)-5-nitro-2-furamide;
8b) N2-(2-{[(1-methyl-4-nitro-1H-2-pyrrolyl)carbonyl]amino}-1,3-benzothiazol-6-yl)-1-methyl-4-nitro-1H-2-pyrrolcarboxamide;
8c) N2-(2-{[(1-methyl-5-nitro-1H-2-imidazolyl)carbonyl]amino}-1,3-benzothiazol-6-yl)-1-methyl-5-nitro-1H-2-imadazolecarboxamide; or
8d) N2-(2-{[(1-methyl-3-nitro-1H-2-pyrazolyl)carbonyl]amino}-1,3-benzothiazol-6-yl)-1-methyl-3-nitro-1H-2-pyrazolecarboxamide.

3. A pharmaceutical composition comprising the compound of claim 1 and a pharmaceutically acceptable carrier.

\* \* \* \* \*